US012577531B2

(12) United States Patent
Park et al.

(10) Patent No.: US 12,577,531 B2
(45) Date of Patent: Mar. 17, 2026

(54) MICROGLIA-SUFFICIENT BRAIN ORGANOIDS

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Dong Shin Park, Singapore (SG); Florent Ginhoux, Singapore (SG); Mahmoud Pouladi, Singapore (SG); Jinqiu Zhang, Singapore (SG)

(73) Assignees: AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 1098 days.

(21) Appl. No.: 17/599,995

(22) PCT Filed: Mar. 30, 2020

(86) PCT No.: PCT/SG2020/050191
§ 371 (c)(1),
(2) Date: Sep. 29, 2021

(87) PCT Pub. No.: WO2020/204827
PCT Pub. Date: Oct. 8, 2020

(65) Prior Publication Data
US 2022/0106563 A1     Apr. 7, 2022

(30) Foreign Application Priority Data
Mar. 29, 2019     (SG) ............................ 10201902893S

(51) Int. Cl.
*C12N 5/079* (2010.01)
*C12N 5/071* (2010.01)
*G01N 33/50* (2006.01)

(52) U.S. Cl.
CPC ......... *C12N 5/0622* (2013.01); *C12N 5/0697* (2013.01); *G01N 33/5082* (2013.01); *C12N 2501/22* (2013.01); *C12N 2502/081* (2013.01); *C12N 2502/1157* (2013.01); *C12N 2506/45* (2013.01); *C12N 2513/00* (2013.01)

(58) Field of Classification Search
None
See application file for complete search history.

(56) References Cited

U.S. PATENT DOCUMENTS

2018/0010096 A1* 1/2018 Lim ................. A61K 39/46433
2019/0046583 A1* 2/2019 Pan ....................... A61K 38/41

FOREIGN PATENT DOCUMENTS

| | | | | |
|---|---|---|---|---|
| CN | 105695410 A | 6/2016 | | |
| WO | WO-2016/109813 A2 | 7/2016 | | |
| WO | WO-2016/114723 A1 | 7/2016 | | |
| WO | WO-2017/117547 A1 | 7/2017 | | |
| WO | WO-2017/123791 A1 | 7/2017 | | |
| WO | WO-2017139638 A1 * | 8/2017 | ............. | A61K 35/30 |
| WO | WO-2017160234 A1 * | 9/2017 | .......... | C12N 5/0018 |
| WO | WO-2018/160496 A1 | 9/2018 | | |

OTHER PUBLICATIONS

Abud et al. iPSC-Derived Human Microglia-like Cells to Study Neurological Diseases (2017) Neuron, 94, pp. 278-293. (Year: 2017).*
Ormel et al, Nature Communications, 2018, 9, 1-14.*
Brownjohn et al., "Functional Studies of Missense TREM2 Mutations in Human Stem Cell-Derived Microglia", Stem Cell Reports, Apr. 10, 2018, vol. 10, No. 4, p. 1294-1307.
Lancaster et al., "Generation of cerebral organoids from human pluripotent stem cells", Nat Protoc, Sep. 4, 2014, vol. 9, No. 10, p. 2329-40.
Lin et al., "APOE4 Causes Widespread Molecular and Cellular Alterations Associated with Alzheimer's Disease Phenotypes in Human iPSC-Derived Brain Cell Types", Neuron, May 31, 2018, vol. 98, No. 6, p. 1141-1154.e7.
Search Report and Written Opinion in International Application No. PCT/SG2020/050191 dated Aug. 25, 2020, 14 pages.
Qian et al., "Brain-Region-Specific Organoids Using Mini-bioreactors for Modeling ZIKV Exposure", Cell, vol. 165, May 19, 2016, pp. 1238-1254.
Raja et al., "Self-Organizing 3D Human Neural Tissue Derived From Induced Pluripotent Stem Cells Recapitulate Alzheimer's Disease Phenotypes", Plos One, DOI:10.1371/journal.pone.0161969, Sep. 13, 2016, 18 pages.
Takata et al., "Induced-Pluripotent-Stem-Cell-Derived Primitive Macrophages Provide a Platform for Modeling Tissue-Resident Macrophase Differentiation and Function", Immunity, vol. 47, Jul. 18, 2017, pp. 183-198.
Kelava et al., "Dishing Out Mini-Brains: Current Progress and Future Prospects in Brain Organoid Research", Developmental Biology, vol. 420, 2016, pp. 199-209.
Abud et al., "iPSC-Derived Human Microglia-like Cells to Study Neurological Diseases", Neuron, vol. 94, Apr. 19, 2017, pp. 278-293.
Invitation to Respond to Written Opinion in International Application No. SG 11202110869Q dated Oct. 21, 2022, 11 pages.
Office Action in EP Application No. 20784356.6 dated Dec. 9, 2022, 12 pages.
Takata et al., "Induced-pluripotent-stem-cell-derived primitive macrophages provide a platform for modeling tissue-resident macrophage differentiation and function", Immunity, Cell Press, vol. 47, No. 1, Jul. 18, 2017, pp. 183-198.

(Continued)

*Primary Examiner* — Peter Paras, Jr.
(74) *Attorney, Agent, or Firm* — MARSHALL, GERSTEIN & BORUN LLP

(57) ABSTRACT

A method for generating a microglia-sufficient brain organoid comprising the step of incubating primitive-like macrophage cells with a brain organoid that is between about 15 to about 30 days old in cerebral organoid medium comprising CSF-1 in a low attachment cell culture vessel to generate microglia cells. The present invention also relates to a microglia-sufficient brain organoid obtained by the method as described herein.

10 Claims, 25 Drawing Sheets

(56) References Cited

OTHER PUBLICATIONS

Muffat et al., "Efficient derivation of microglia-like cells from human pluripotent stem cells", Nature Medicine, vol. 22, No. 11, Sep. 26, 2016, pp. 1358-1367.

Haenseler et al., "A Highly efficient human pluripotent stem cell microglia model displays a neuronal-co-culture-specific expression profile and inflammatory response", Stem Cell Reports, vol. 8, No. 6, Jun. 6, 2017, pp. 1727-1742.

Abud et al., "iPSC-Derived human microglia-like cells to study neurological diseases", Neuron, vol. 94, No. 2, Apr. 19, 2017, pp. 278-293.

Speicher et al., "Generating microglia from human pluripotent stem cells: novel in vitro models for the study of neurodegeneration", Molecular Neurodegeneration, vol. 14, No. 1, Dec. 1, 2019, 16 pages.

Song et al., "Functionalization of brain region-specific spheroids with isogenic microglia-like cells", Scientific Reports, vol. 9, No. 1, Jul. 30, 2019, 18 pages.

Sabate-Soler et al., "Microglia integration into human midbrain organoids leads to increased neuronal maturation and functionality", GLIA, vol. 70, No. 7, Jun. 1, 2022, pp. 1267-1288.

Second Office Action in CN Application No. 2020800398493 dated Jun. 28, 2024, 17 pages.

First Office Action in CN Application No. 2020800398493 dated Nov. 30, 2023, 26 pages.

* cited by examiner

SOX2 NESTIN IBA1

Organoid alone    iMac alone    Co-culture

Digestion into single cells

Single-cell transcriptomics

Organoid alone

GO analysis on the proteins up-regulated in co-iMacs (PLIN2)
LIPID DROPLET PLIN2 GFP DAPI

MICROGLIA-SUFFICIENT BRAIN ORGANOIDS

CROSS-REFERENCE TO RELATED APPLICATIONS

This application claims the benefit of priority of Singapore application No. 10201902893S, filed 29 Mar. 2019, the contents of it being hereby incorporated by reference in its entirety for all purposes.

FIELD OF THE INVENTION

The present invention relates generally to the field of cell culture. In particular, the present invention relates to the use of a method for generating a microglia-sufficient brain organoid.

BACKGROUND OF THE INVENTION

Microglia are the resident immune cells of the central nervous system. These brain-resident macrophages account for 5-10% of the total cells found in the brain and play important roles in brain development, homeostasis and pathologies. Microglia survey the brain and contribute to innate immune responses upon injury. Moreover, microglia constantly interact with neuronal synapses contributing to synaptic remodeling and axon outgrowth. However, the majority of studies on microglia have been performed on animal models, due to a lack of adequate human model systems that recapitulate the development of microglia in vivo. Human model systems, however, will be vital to understand how microglia impacts human central nervous system development, physiology and pathology.

With recent advances in stem cell technologies, it is now possible to generate human induced pluripotent stem cell (iPSC)-derived three dimensional brain organoids that mimic the human embryonic brain to a certain extent. These brain organoids have been shown to develop neuroepithelial rosettes that resemble the developing cerebral cortex. Furthermore, intermediate progenitor cells (TBR2-positive) and different subtypes of cortical neurons (TBR1-, CTIP-, SATB2- and CUX1-positive) have also been observed in the brain organoids. Transcriptomic studies have further shown that the neuronal cell types generated in these organoids are similar to the endogenous counterparts in the human embryonic brain. However, despite these similarities, current brain organoids still fail to fully recapitulate the human embryonic brain as most lack microglia which are essential for brain development and maturation. Methods to generate brain organoids have generated inconsistent results in terms of the emergence of microglia in these organoids. This has impeded microglia research aiming to decipher the role of human microglia during the early stages of brain development.

There is therefore a need to develop methods for generating brain organoids that comprise microglia cells.

SUMMARY

In one aspect, there is provided a method for generating a microglia-sufficient brain organoid comprising the step of incubating primitive-like macrophage cells with a brain organoid that is between about 15 to about 30 days old in cerebral organoid medium comprising CSF-1 in a low attachment cell culture vessel to generate microglia cells.

In another aspect, there is provided a microglia-sufficient brain organoid obtained by the method as described herein.

In another aspect, there is provided a method for screening a compound that targets microglia function comprising the steps of contacting the microglia-sufficient brain organoid as described herein with said compound and analysing the microglia cell for a predetermined trait.

In another aspect, there is provided a method for screening a compound to treat a neurodegenerative disease comprising the step of contacting the microglial-sufficient brain organoid as described herein with said compound and analysing the microglia cell for a predetermined trait.

In another aspect, there is provided a kit when used in the method as described herein, comprising cerebral organoid medium comprising CSF-1 together with instructions for use.

In another aspect, there is provided a method of isolating one or more predetermined populations of cells from a microglia-sufficient brain organoid comprising the steps of:

a) incubating the microglia-sufficient brain organoid in a digestion solution at 37° C. for about 30 minutes;

b) physically agitating the microglia-sufficient brain organoid from step a);

c) subjecting the microglia-sufficient brain organoid from step b) to heat treatment at 1400 rpm for 10 minutes at 37° C.;

d) physically agitating the microglia-sufficient brain organoid from step c);

e) incubating the microglia-sufficient brain organoid from step d) at room temperature to allow debris to settle;

f) collecting the digestion solution;

g) isolating the one or more predetermined populations of cells from the digestion solution.

Definitions

The term "organoid" as used in the context of this application refers to a three-dimensional cellular structure that mimics the organization and function of organs. Organoids consist of tissue-specific cell types that self-organize through cell sorting and spatially restricted lineage commitment. Organoids may be derived from stem cells, such as embryonic stem cells or induced pluripotent stem cells. The terms "brain organoid" and "cerebral organoid", which are used interchangeably in this specification, refer to an organoid that has anatomical features that resemble that of a brain. It will generally be understood that a brain organoid or cerebral organoid is comprised of various cell types of the brain. These cell types may have different developmental potential, with some cell types being less differentiated than others.

As used herein, the term "microglia" refers to a type of glial cell involved in the mediation of an immune system within the central nervous system. These cells are constituent cells of the central nervous system present in the brain. Microglia constitute 20% of the total glial cell population within the brain. Microglia play a crucial role during healthy central nervous system development and are involved in the initiation, progression and clearance of diseases affecting the central nervous system. Microglia are known to selectively colonize the cortical proliferative zones and to phagocytose neural precursor cells. Microglia are also known for their ability to phagocytose amyloid beta peptides. The term "iMicros" as used herein refers to cells that mimic microglia cells found in vivo. iMicros can be generated by co-culturing primitive macrophages or primitive-like macrophages with brain organoids. The terms "iMicros" and "microglia-like cells" may be used interchangeably. It will generally be understood that microglia-like cells are substantially similar to microglia cells in terms of phenotype, genotype and function. Similar to microglia, microglia-like cells are able to engulf amyloid beta peptides and extend their dendrites upon the physical damage. Microglia-like cells also display amoeboid morphology in the brain organoids, which is a typical morphology displayed by microglia in the embryonic brain during the early stage of brain development. Microglia-like cells also express microglia-specific markers such as TMEM119, P2RY12, Sall1 and Merk. The term "microglia-sufficient brain organoid" as used herein refers to a brain organoid that comprises microglia cells or microglia-like cells. The microglia-sufficient brain organoid may be a forebrain organoid, a midbrain organoid or a hindbrain organoid. The forebrain organoid may be a hypothalamus organoid.

The term "stem cell" as used herein refers to a cell capable of self-replication and that are capable of differentiating into more specialized cells. Stem cells may include but are not limited to embryonic stem cells, adult stem cells and induced pluripotent stem cells. A pluripotent stem cell is one that is able to differentiate into any of the three germ layers: the endoderm, the mesoderm or the ectoderm. "Embryonic stem cells" are pluripotent stem cells of the inner cell mass of a blastocyst. "Induced pluripotent stem cells" are pluripotent stem cells artificially derived from a non-pluripotent cell, which may be an adult somatic cell. The stem cells as used herein may include but are not limited to human, non-human primate, murine and avian stem cells.

As used herein, the term "differentiate" refers to the developmental process by which a cell has progressed further down a developmental pathway than its immediate precursor cell. A differentiated cell is a cell of a more specialized cell type derived from a cell of a less specialized cell type in a cellular differentiation process. A differentiated cell is one that has taken on a more committed position within the lineage of the cell.

As used herein, the term "neural progenitor cell" (NPC) refers to non-mature cells of the nervous system which can differentiate into neurons and glial cells. NPCs express phenotypic markers characteristic of the neural lineage including CD271, Nestin, PAX6, SOX1, SOX2, VIM and HES2. NPCs may be found in brain organoids along with other cell types such as neurons and glial cells. Co-NPCs refer to NPCs of the brain organoid that are co-cultured with iMacs.

The term "cell culture", for the purposes of this application, refers to the process by which cells are grown under controlled conditions in vitro that mimic their natural environment. Cell culture conditions vary for each cell type, but may consist of a suitable vessel with one or more substrates or one or more media that supply the essential nutrients required for cell growth and that regulate the physio-chemical environment. Two or more cell types may be incubated together in a co-culture where the two- or more cell types are maintained in conditions suitable for their mutual growth. The two or more cell types may be grown on the same surfaces or on different surfaces. When two or more cell types are co-cultured, or incubated in the same cell culture, the cells are able to interact such that secreted soluble mediators produced by a cell can interact with another cell.

The term "macrophage" in the context of this specification refers to specialized cells involved in the detection, phagocytosis and destruction of bacteria and other harmful organisms. Macrophages play a significant part in immunity and immune responses. Primitive macrophages are generated in the yolk sac from early erythro-myeloid progenitors and further differentiate into microglia. The term "iMacs" as used herein refers to cells that mimic primitive macrophages found in vivo. The terms "iMacs" and "primitive-like macrophages" may be used interchangeably. iMacs or primitive-like macrophages can be derived from pluripotent cells, such as iPSC or ESC. It will generally be understood that primitive-like macrophages are substantially similar to primitive macrophages in terms of phenotype, genotype and function. Similar to primitive macrophages, primitive-like macrophages exhibit phagocytic ability and, upon LPS stimulation, release pro-inflammatory cytokines such as TNF-$\alpha$, IL-1$\beta$ and IL-6. The term "co-iMacs" as used herein refer to iMacs co-cultured with the brain organoid.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1A:
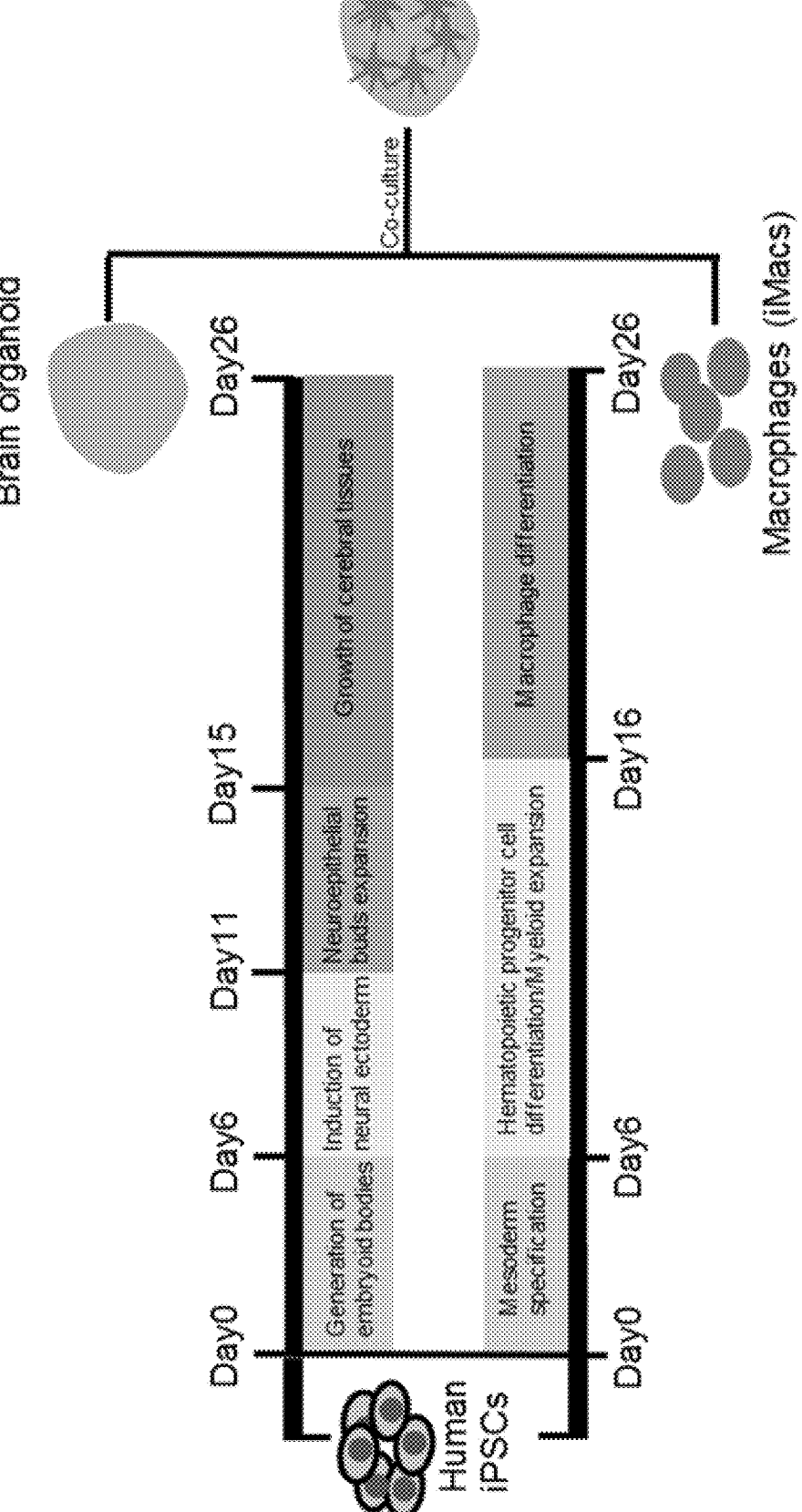
FIG. 1 shows the characterization of iMacs (iPSC-derived primitive-like macrophages) in the brain organoids. A) shows a schematic overview of generating microglia-sufficient brain organoids. In B), the brain organoid was co-cultured with iMacs for 18 days, cleared by benzyl alcohol and benzyl benzoate (BABB) and imaged entirely in 3D. Boxed area highlighted on right. Arrowhead, clusters of iMacs on organoid. C), the sectioning and immunohistochemistry of co-cultured brain organoid reveals the presence of iMacs in the organoid. Boxed area highlighted on right. In D), immunohistochemical staining for Ki67 reveals that some of iMacs in the organoid are Ki67 positive suggesting their proliferative capacity in the organoid. E) shows that GFP-positive iMac elongates its dendrites towards the neuronal injury induced by two-photon laser ablation. F) shows that GFP-positive iMacs actively move in the organoid and some of them contain Ab1-42 peptide-TAMRA suggesting their ability to survey the organoid and phagocytose the peptides. Boxed area highlighted on right.

In a first aspect, the present invention refers to a method for generating a microglia-sufficient brain organoid comprising the step of incubating primitive-like macrophage cells with a brain organoid that is between about 15 to about 30 days old in cerebral organoid medium comprising CSF-1 in a low attachment cell culture vessel to generate microglia cells. The low attachment cell culture vessel may be a low attachment multiple well plate or an ultra-low attachment multiple well plate. It is generally understood in the art that a low attachment or ultra-low attachment cell culture vessel or plate is one that inhibits attachment of cells onto the vessel or plate. Low attachment or ultra-low attachment may be achieved by various means, such as by coating the vessel or plate with a compound that inhibits cell attachment. In one embodiment, the low attachment cell culture vessel is a Corning® Costar® Ultra-Low Attachment Multiple Well Plate.

In one embodiment, the brain organoid is between about 23 to 29 days old from the pluripotent state. This will be understood to mean that pluripotent cells have been differentiated for about 23 to 29 days old to generate the brain organoid. In a preferred embodiment, the brain organoid is about 26 days old from the pluripotent state.

In one embodiment, the cerebral organoid medium comprises about 25-100 ng/ml CSF-1. In a further embodiment, the cerebral organoid medium comprises 100 ng/ml CSF-1.

In one embodiment, less than about 200,000 primitive-like macrophages are incubated with the brain organoid. In a further embodiment, about 150,000 or less primitive-like macrophages are incubated with the brain organoid.

In one embodiment, the step of incubating primitive-like macrophage cells and brain organoid takes place for at least 1 week. The primitive-like macrophage cells and brain organoid may be incubated together for about 1 week, about 2 weeks, about 3 weeks, about 4 weeks, about 5 weeks, about 6 weeks, about 7 weeks, about 8 weeks, about 9 weeks, about 10 weeks, about 11 weeks or about 12 weeks. The length of incubation will depend on the desired end-point of the experiment.

In one embodiment, the incubation or co-culture of primitive-like macrophage cells with the brain organoid causes the primitive-like macrophage cells to differentiate into microglia cells. In one embodiment, the incubation or co-culture of iMacs with the brain organoid causes the iMacs to differentiate into iMicros.

Longer co-culture may allow the observation of long-term effects of co-culture in normal and disease conditions. Longer co-culture may be used to observe the effects of drug screening.

The differentiation of primitive-like macrophage cells into microglia cells may be measuring by testing the ability of the microglia cells to respond to injury in the brain or to phagocytose amyloid beta peptides. The differentiation into microglia cells can also be measured by quantifying the expression level of microglia-specific markers such as TMEM119, P2RY12, Sall1 and Merk.

The incubation of primitive-like macrophage cells with the brain organoid may have an effect on the size of the organoid, the number and proportion of NPCs in the organoid, the maturation of NPCs and the lipid distribution in the organoid. For example, the incubation of primitive-like macrophage cells with the brain organoid may decrease the size of the organoids and the number of NPCs in the organoid. In one embodiment, the incubation of primitive-like macrophage cells with the brain organoid may cause genes involved in cell proliferation to be downregulated in NPCs. These genes include but are not limited to TOP2A, CEMPF, CDC20 and UBE2C.

The incubation of primitive-like macrophage cells with the brain organoid may promote maturation of NPCs. In one embodiment, the primitive-like macrophage cells may upregulate genes implicated in axon outgrowth and neurogenesis. These genes may include but are not limited to IL-1b, IL 10, NRG1, SEMA4C, VEGFA and ADAMS. In another embodiment, the incubation of primitive-like macrophage cells with the brain organoid may cause NPCs to exhibit axons that are longer and more numerous.

The incubation or co-culture of primitive-like macrophage cells with the brain organoid may modify the lipid distribution in the organoids and the lipid content in NPCs. In one embodiment, the incubation of primitive-like macrophage cells with the brain organoid may cause genes involved in lipid droplet formation and in lipid export to be upregulated in the primitive-like macrophage cells. These genes may include but are not limited to PLIN2, M1D1P1, ARL4C, SEPT9 and ABCA1. In another embodiment, NPCs in co-cultured brain organoids display a higher neutral lipid content.

In one embodiment, the cells of the microglia-sufficient brain organoid generated by the method as described herein are dissociated and one or more predetermined populations of cells are isolated. The predetermined populations of cells may include but are not limited to neurons, neuronal progenitor cells and glial cells.

In one embodiment, the one or more predetermined populations of cells are isolated using fluorescence activated cell sorting (FACS) or magnetic activated cell sorting (MACS).

In one embodiment, the primitive-like macrophage cells used in the method as described herein are generated from a first population of stem cells by:

i) incubating said stem cells in a culture medium comprising a GSK3 inhibitor, BMP4 and VEGF to differentiate said stem cells into cells of the mesoderm lineage;

ii) incubating said cells of the mesoderm lineage in a culture medium comprising FGF-2 to differentiate said cells of the mesoderm lineage into hemangioblast cells;

iii) incubating said hemangioblast cells in a culture medium comprising VEGF and FGF-2;

iv) incubating said hemangioblast cells in a culture medium comprising DKK1, SCF, FGF2, IL3 and IL6 to differentiate said hemangioblast cells to hematopoietic cells;

v) incubating said hematopoietic cells in a culture medium comprising SCF, FGF-2, IL-3 and IL-6 to induce maturation of said hematopoietic cells;

vi) incubating said matured hematopoietic cells in a culture medium comprising CSF-1 to differentiate said matured hematopoietic cells to primitive-like macrophage cells.

In one embodiment, in step i), the GSK3 inhibitor is CHIR99021 and the stem cells are incubated for up to 2 days to differentiate said stem cells into cells of the mesoderm lineage.

In another embodiment, in step ii), the cells of the mesoderm lineage are incubated for up to 4 days to differentiate said cells of the mesoderm lineage into hemangioblast cells.

In yet another embodiment, steps iii) and iv) take place over a period of up to 10 days.

In yet another embodiment, in step vi), the matured hematopoietic cells are incubated for up to 10 days to differentiate said matured hematopoietic cells into primitive-like macrophage cells.

In one embodiment, the primitive-like macrophages are generated over a period of 26 days.

In one embodiment, the brain organoid used in the method as described herein is generated from a second population of stem cells by:

i) incubating said second population of stem cells in a low attachment cell culture vessel to form an embryoid body (EB);

ii) incubating said embryoid body in neural induction medium to differentiate said embryoid body into an organoid comprising neuroectoderm cells;

iii) embedding the organoid comprising neuroectoderm cells in Matrigel and incubating the organoid comprising neuroectoderm cells in cerebral organoid medium containing N2 and B27 without vitamin A to differentiate said organoid comprising neuroectoderm cells to an organoid comprising neural epithelial cells;

iv) incubating the organoid comprising neural epithelial cells with cerebral organoid medium containing N2 and B27 with vitamin A to differentiate said organoid comprising neural epithelial cells to said brain organoid.

In one embodiment, in step i) of the method of generating the brain organoid from a second population of stem cells, the low attachment cell culture vessel is a U-bottom plate and the second population of stem cells is incubated for up to 6 days to form an embryoid body (EB).

In another embodiment, in step ii) of the method of generating the brain organoid from a second population of stem cells, the EB is incubated for up to 6 days to differentiate the EB into the organoid comprising neuroectoderm cells.

In yet another embodiment, in step iii) of the method of generating the brain organoid from a second population of stem cells, the organoid comprising neuroectoderm cells are incubated in cerebral organoid medium containing B27 without vitamin A for up to 4 days to differentiate said organoid comprising neuroectoderm cells to said organoid comprising neural epithelial cells.

In another embodiment, the Matrigel is removed from the organoid comprising neural epithelial cells prior to or during step iv) of the method of generating the brain organoid from a second population of stem cells.

In yet another embodiment, in step iv) of the method of generating the brain organoid from a second population of stem cells, the organoid comprising neural epithelial cells is incubated with cerebral organoid medium containing B27 with vitamin A for up to 26 days to differentiate said organoid comprising neural epithelial cells to the brain organoid.

In one embodiment, the organoid comprising neural epithelial cells is incubated with shaking at 85 rpm to differentiate said organoid comprising neural epithelial cells to the brain organoid.

In one embodiment, the brain organoid is generated from the second population of stem cells over a period of between about 15 to 30 days. In another embodiment, the brain organoid is generated over a period of between about 23 to 29 days. In a preferred embodiment, the brain organoid is generated over a period of about 26 days.

In one embodiment, the first and second populations of stem cells are embryonic stem cells (ESC), induced pluripotent stem cells (iPSC) or combinations thereof. In one embodiment, the first and second populations of stem cells are human induced pluripotent stem cells. The first and second populations of stem cells may be the same or different stem cells. In one embodiment, the first and second populations of stem cells are the same stem cells.

In one aspect, the present invention provides for a microglia-sufficient brain organoid obtained by the method as described herein. The microglia-sufficient brain organoid may comprise microglia-like cells that express microglia-specific markers such as TMEM119, P2RY12, Sall1 and Merk.

In another aspect, the present invention provides for a method for screening a compound that targets microglia function comprising the steps of contacting the microglia-sufficient brain organoid as described herein with said compound and analysing the microglia cell for a predetermined trait.

In one embodiment, the method of screening a compound that targets microglia function involves contacting the compound with microglia-sufficient organoids and comparing these organoids with organoids that have not been contacted with the compound. This method may further comprise downstream analysis including functional studies (neuron firing activities, microglia engulfment of amyloid beta peptides and their response to physical damange), single RNA sequencing, and analyses of metabolic changes that can contribute to neuronal diseases.

In one aspect, the present invention provides for a method for screening a compound to treat a neurodegenerative disease comprising the step of contacting the microglial-sufficient brain organoid as described herein with said compound and analysing the microglia cell for a predetermined trait.

In one embodiment, the method of screening a compound to treat a neurodegenerative disease involves contacting the compound with microglia-sufficient organoids and comparing these organoids with orgaonids that have not been contacted with the compound. This method may further comprise downstream analysis including functional studies (neuron firing activities, microglia engulfment of amyloid beta peptides and their response to physical damange), single RNA sequencing, and analyses of metabolic changes that can contribute to neuronal diseases.

The predetermined trait may be a morphological feature, a flow cytometry profile, a gene expression profile, a distribution pattern of microglia cells, or combinations thereof.

In one aspect, the present invention provides for a kit when used in the method as described herein, comprising cerebral organoid medium comprising CSF-1 together with instructions for use.

In one embodiment, the kit as described herein further comprises a
  a) a first culture medium comprising a GSK3 inhibitor, BMP4 and VEGF;
  b) a second culture medium comprising BMP4, VEGF and FGF-2;
  c) a third culture medium comprising VEGF and FGF-1;
  d) a fourth culture medium comprising VEGF, DKK1, SCF, FGF-2, IL-3 and IL-6;
  e) a fifth culture medium comprising FGF, IL6, IL3 and SCF; and
  f) a sixth culture medium comprising CSF-1;
to generate primitive-like macrophage cells from a first population of stem cells; and
  g) a neural induction medium;
  h) a cerebral organoid medium containing N2 and B27 without vitamin A; and
  i) a cerebral organoid medium containing N2 and B27 with vitamin A; to generate brain organoids from a second population of stem cells.

In one aspect, the present invention provides for a method of isolating one or more predetermined populations of cells from a microglia-sufficient brain organoid comprising the steps of:
  a) incubating the microglia-sufficient brain organoid in a digestion solution at 37° C. for about 30 min;
  b) physically agitating the microglia-sufficient brain organoid from step a);
  c) subjecting the microglia-sufficient brain organoid from step b) to heat treatment at 1400 rpm for 10 min at 37° C.;

d) physically agitating the microglia-sufficient brain organoid from step c);
  e) incubating the microglia-sufficient brain organoid from step d) at room temperature to allow debris to settle;
  f) removing the digestion solution;
  g) isolating the one or more predetermined populations of cells from the digestion solution.

In one embodiment, steps c) to f) are repeated at least two more times.

In another embodiment, the digestion solution is filtered and centrifuged prior to step g).

In one embodiment, the one or more predetermined populations of cells are isolated by FACS or MACS. The one or more predetermined populations of cells may include but are not limited to neurons, neuronal progenitor cells, glial cells and primitive-like macrophage cells.

In another embodiment, the digestion solution is accutase and collagenase at a ratio of 9:1.

In one embodiment, the digestion solution from step g) is filtered and subjected to downstream experiments. The downstream experiments may include but are not limited to flow cytometry, sorting and immunostaining.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Materials and Methods

Human iPSC-Derived Macrophage Generation

In order to generate human iMacs, in the first step (days 0-6), a modified protocol was used to recreate mesoderm specification and induce human hemangioblast-like cell formation, with the addition of CHIR99021. Human iPSC colonies were specified to the mesoderm by incubation with BMP-4 and VEGF, and their differentiation boosted by incubation with CHIR99021 during the first 2 days of differentiation. Hemangioblast formation was induced by adding FGF-2 instead of the CHIR99021 (days 2-4) and then maintained with VEGF and FGF-2 (days 4-6). In the next step (days 6-10), the commitment of the hemangioblast toward hematopoietic cells was induced, with the notable addition of DKK1, a Wnt antagonist to inhibit Wnt signaling for the promotion of primitive hematopoiesis. Hematopoietic cells were matured by continued incubation with SCF, FGF-2, IL-3 and IL-6, which was added to promote hematopoietic maturation and CSF-1R expression (days 12-16). From day 16, terminal differentiation to human iMacs was initiated by exposure to CSF-1. In more details, human iPSCs (HD33i) were cultured to 75% confluency, then digested with 1 mg/mL collagenase (GIBCO, 17104-019) for 20 minutes. The cells were collected by mechanical scrapping, generating aggregates between 50 to 200 um, centrifuged at 300 g, resuspended in mTesrl and passaged at a ratio of 1:25 (roughly $1.0 \times 10^5$ cells) on to a Matrigel-coated 6 well plate. Starting from the next day, with a full media change every other day, the cells were cultured for the next 16 days in Stempro Medium, supplemented with the following cytokines during the differentiation process: Differentiation Day 0 (5 ng/mL BMP4, 50 ng/mL VEGF, and 2 uM CHIR99021), Differentiation Day 2 (5 ng/mL BMP4, 50 ng/mL VEGF, and 20 ng/mL FGF2), Differentiation Day 4 (15 ng/mL VEGF and 5 ng/mL FGF2), Differentiation Day 6 to 10 (10 ng/mL VEGF, 10 ng/mL FGF2, 50 ng/mL SCF, 30 ng/mL DKK-1 (RnD, 5439-DK), 10 ng/mL IL-6 (RnD, 206-IL), and 20 ng/mL IL-3), Differentiation Day 12 and 14 (10 ng/mL FGF2, 50 ng/mL SCF, 10 ng/mL IL-6, and 20 ng/mL IL-3). From Differentiation Day 16, the cells were switched to SF-Diff supplemented with 50 ng/mL CSF-1, and full medium change was done every 3 days up to Differentiation Day 25, when the floating cells were used for experiments. The cells were also cultured in a hypoxia incubator for the first 8 days, set to 5% CO2 and 5% O2, and were cultured in a normal incubator after Differentiation Day 8. Floating cells typically appeared around Differentiation Day 7, and were collected and re-plated on to the basement cells during medium changes.

Generating iPSC-Derived Brain Organoids

The three-dimensional brain organoids were generated using the following protocol. From Day 0-6, embryoid bodies (EBs) were formed by culturing the human iPSCs in a low attachment U-bottom 96-well plate containing hESC medium. From Day 6-11, neuroectoderm formation was induced by culturing the EBs in neural induction medium. From Day 11-15, neural epithelium formation was induced by embedding the organoids in matrigel and culturing them in cerebral organoid medium (containing B27 without vitamin A) in a 10 cm dish. From Day 15-26, the medium was changed to cerebral organoid medium (containing B27 with vitamin A) and the 10 cm dish containing the organoids were placed on the shaker at 85 rpm to induce the cerebral tissue formation.

Generation of Dorsal and Ventral Forebrain Organoids and Co-Culture with iMacs

Dorsal forebrain organoids (hCS) were generated from human iPSCs according to the protocol described by Birey et al 2017. On Day 0, human iPSCs colonies were transferred to ultra-low-attachment 10 cm dish containing 15 ml hPS medium supplemented with Dorsomorphin (5 uM), SB-431542 (10 uM) and rock inhibitor (10 uM). From Day 2, the medium (without Rock inhibitor) was changed every day until Day 5. On Day 6, the medium was changed with neural medium (NM) supplemented with EGF2 (20 ng/ml) and FGF2 (20 ng/ml) for the next 19 days (with daily medium change in the first 10 days, and every other day medium changes for the subsequent 9 days). From Day 25, FGF2 and EGF were replaced with BDNF (20 ng/ml) and NT3 (20 ng/ml) (with media changes every other day). From Day 43, NM without growth factors was used for medium changes every four days. Ventral forebrain organoids (hSS) were generated from human iPSCs according to the protocol described by Birey et al 2017. The same protocol was used as dorsal organoid except that IWP-2 (5 uM) was added from day 4 to day 23, while SAG (100 nM) was added from day 12 to day 23. The ventral forebrain organoid was co-cultured with GFP-positive iMacs for 2 weeks then fused with dorsal forebrain organoid. To fuse the dorsal and ventral forebrain organoids, the organoids were placed in a 1.5 ml microcentrifuge tube and incubated for 3 days with medium change at day 2. After fusion, the organoids were transferred to the Iwaki plate. The Matrigel was used to stabilize the organoid on the Iwaki plate. The live image was taken using a confocal laser scanning microscope (Olympus, Japan) and analyzed with Imaris Software (BITPLANE).

Culture of Forebrain Organoids from Human iPSCs

To generate forebrain-specific organoids, human iPSC colonies were detached 7 days after passage with Collagenase Type IV, washed with fresh stem cell medium and cultured in a 15 ml conical tube. On day 1, detached and washed iPSC colonies were transferred to an Ultra-Low attachment 6-well plate (Corning Costar), containing 3 ml of stem cell medium (without FGF-2), plus 2 µM Dorsomorphine (Sigma) and 2 µM A83-01 (Tocris). On days 5-6, half of the medium was replaced with induction medium consisting of DMEM:F12, 1× N2 Supplement (Invitrogen), 10 µg/ml Heparin (Sigma), 1× Penicillin/Streptomycin, 1× Non-essential Amino Acids, 1× Glutamax, 4 ng/ml WNT-3A (R&D Systems), 1 µM CHIR99021 (Cellagentech), and 1 µM SB-431542 (Cellagentech). On day 7, organoids were embedded in Matrigel (BD Biosciences) and continued to grow in induction medium for 6 more days. On day 14, embedded organoids were mechanically dissociated from Matrigel by pipetting up and down onto the plate with a 5 ml pipette tip. Typically, 10-20 organoids were transferred to each well of a 12-well spinning bioreactor (SpinΩ) containing differentiation medium, consisting of DMEM:F12, 1× N2 and B27 Supplements (Invitrogen), 1× Penicillin/Streptomycin, 1× 2-Mercaptoenthanol, 1× Non-essential Amino Acids, 2.5 µg/ml Insulin (Sigma). At day 71, differentiation medium was exchanged with maturation medium, consisting of Neurobasal (Gibco), 1× B27 Supplement, 1× Penicillin/Streptomycin, 1× 2-Mercaptoenthanol, 0.2 mM Ascorbic Acid, 20 ng/ml BDNF (Peprotech), 20 ng/ml GDNF (Peprotech), 1 ng/ml TFGβ (Peprotech), and 0.5 mM cAMP (Sigma). The organoids could grow beyond 110 days in maturation medium. All media were changed every other day. For the stationary culture, day 14 organoids were generated following the same protocol and then maintained in an Ultra-Low attachment 6 well plate (Corning Costar) with differentiation media.

Culture of Midbrain Organoids from Human iPSCs

To generate midbrain-specific organoids, human iPSC colonies were detached with Collagenase Type IV 7 days after passage and washed with fresh stem cell medium in a 15 ml conical tube. On day 1, the detached and washed iPSC colonies were transferred to an Ultra-Low attachment 6-well plate containing EB medium, consisting of DMEM:F12, 15% Knockout Serum Replacer, 1× Glutamax, 1× 2-Mercaptoenthanol, 100 nM LDN-193189, 10 µM SB-431542, 100 ng/ml SHH (Peprotech), 2 µM Purmorphamine (Stemgent), 100 ng/ml FGF-8 (Peprotech). On day 5, EB medium was gradually switched to SHH medium, consisting of DMEM:F12, 1× N2 Supplement, 1× Glutamax, 100 nM LDN-193189, 3 µM CHIR99021, 100 ng/ml SHH, 2 µM Purmorphamine, 100 ng/ml FGF-8. On day 7, SHH medium was replaced with induction medium, consisting of DMEM: F12, 1× N2 Supplement, 1× Glutamax, 100 nM LDN-193189, 3 µM CHIR99021. On day 14, 10-20 organoids were transferred to SpinΩ with differentiation medium, consisting of Neurobasal, 1× B27 Supplement, 1× Glutamax, 1× 2-Mercaptoenthanol, 20 ng/ml BDNF, 20 ng/ml GDNF, 0.2 mM Ascorbic Acid, 1 ng/ml TGFβ, and 0.5 mM c-AMP. All media were changed every other day.

Culture of Hypothalamus Organoids from Human iPSCs

To generate hypothalamus-specific organoids, human iPSC colonies were detached 7 days following passaging with Collagenase Type IV, and washed with fresh stem cell medium in a 15 ml conical tube. On day 1, detached and washed iPSC colonies were transferred to an Ultra-Low attachment 6-well plate (Corning Costar) containing stem cell medium. One day after (day 2), stem cell medium was replaced with induction medium A, consisting of DMEM: F12, 10% Knockout Serum Replacer, 1× Non-essential Amino Acids, 1× Penicillin/Streptomycin, 1× 2-Mercaptoenthanol, 1× Glutamax, 2.5 µM LDN-193189 (Stemgent), 3 µM SB-431542, and 450 µM 1-Thioglycerol (Sigma). On day 4, the medium was switched to induction medium B, consisting of DMEM:F12, 10% Knockout Serum Replacer, 1× Non-essential Amino Acids, 1× Penicillin/Streptomycin, 1× Glutamax, 1× N2 Supplement, 10 ng/m Wnt-3A, 20 ng/ml SHH and 2 µM Purmorphamine. On day 7, 5-10 organoids were transferred to a 12-well spin bioreactor and induction medium B was replaced with differentiation medium, consisting of DMEM:F12/Neurobasal (1:1 ratio), 1× B27 Supplement, 1× Non-essential Amino Acids, 1× Penicillin/Streptomycin, 1× Glutamax, 10 ng/ml FGF-2 and 10 ng/ml CTNF (Peprotech). Media were changed every other day.

Reagent Setup for Neural Induction Medium

DMEM-F12 was combined with 1% N2 supplement (vol/vol), 1% Glutamax supplement (vol/vol) and 1% MEM-NEAA (vol/vol). Heparin was added (final concentration 1 µg ml$^{-1}$) and the medium was filtered using a vacuum driven 0.2 µm filter unit.

Reagent Setup for Cerebral Organoid Differentiation Medium

For approximately 250 ml of medium, 125 ml DMEM-F12 was combined with 125 ml Neurobasal, 1.25 ml N2 supplement, 62.5 µl Insulin, 2.5 ml Glutamax supplement, 2.5 ml MEM-NEAA and 2.5 ml penicillin-streptomycin. A 1:100 dilution of 2-Mercaptoethanol in DMEM-F12 was prepared and 87.5 µl of this was added to the medium. 2.5 ml B27 supplement was added.

Digestion Protocol to Isolate One or More Predetermined Populations of Cells from a Microglia-Sufficient Brain Organoid The organoid was placed in a 1.5 ml Eppendorf tube containing 0.6 ml of digestion solution containing accutase and collagenase mixed at a ratio of 9:1. After incubation at 37° C. for 30 minutes, the mixture was agitated by pipetting 10 times up and down gently using a 1 ml pipette tip to release the cells from the organoid. The mixture was placed in a heat block at 1400 rpm for 10 minutes at 37° C. to further release the cells from the organoid. The mixture was agitated by pipetting 10 times up and down gently using a 1 ml pipette tip to further release the cells from the organoid. The mixture was incubated at room temperature to allow the debris to settle at the bottom of the tube and the supernatant, which contains the digested cells, was collected. New digestion solution was added into the tubes containing the debris. The tubes were subjected to another round of heat block treatment and pipetting to collect more single cells from the supernatant (digestion solution). The collected supernatant was filtered through 70 um filter paper, centrifuged and stained with antibodies for FACS. Neurons, neuronal progenitor cells, glial cells and primitive-like macrophage cells (iMacs) were able to be separated using FACs.

Example 1

Primitive-Like Macrophages (iMacs) Colonize Brain Organoid and Differentiate in Functionally Active Microglia-Like Cells (iMicros)

Cerebral organoids and primitive-like macrophages (iMacs) were generated from the same human iPSCs using the protocol shown in FIG. 1A. Microglia are observed in the human embryonic brain as early as 4.5 weeks after conception. iMacs were co-cultured with relatively young brain organoids (Day 26) that mimic the embryonic brain at the first trimester stage. The co-culture was carried out using organoid growth medium supplemented with 100 ng/ml CSF-1, with half medium change every three days. In addition, the ultra-low 24 attachment plate that was used for co-culture minimized the attachment of iMacs onto the plate thus maximizing their physical interactions with the organoids. In addition, one organoid was cultured per well which ensured enough space and nutrients for it to survive and grow.

Figure 1B:
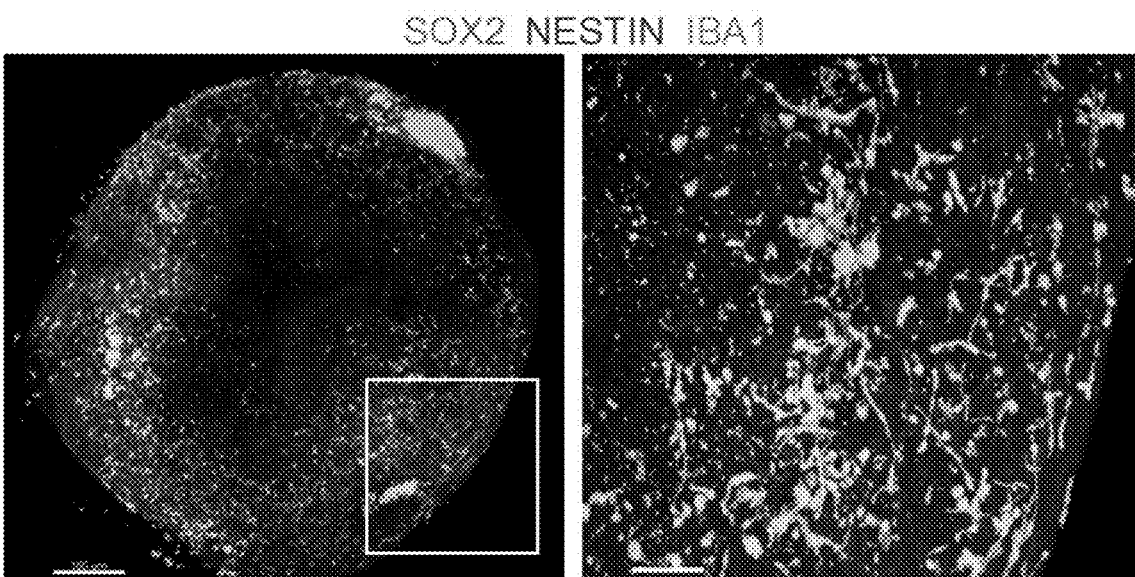
Figure 1C:
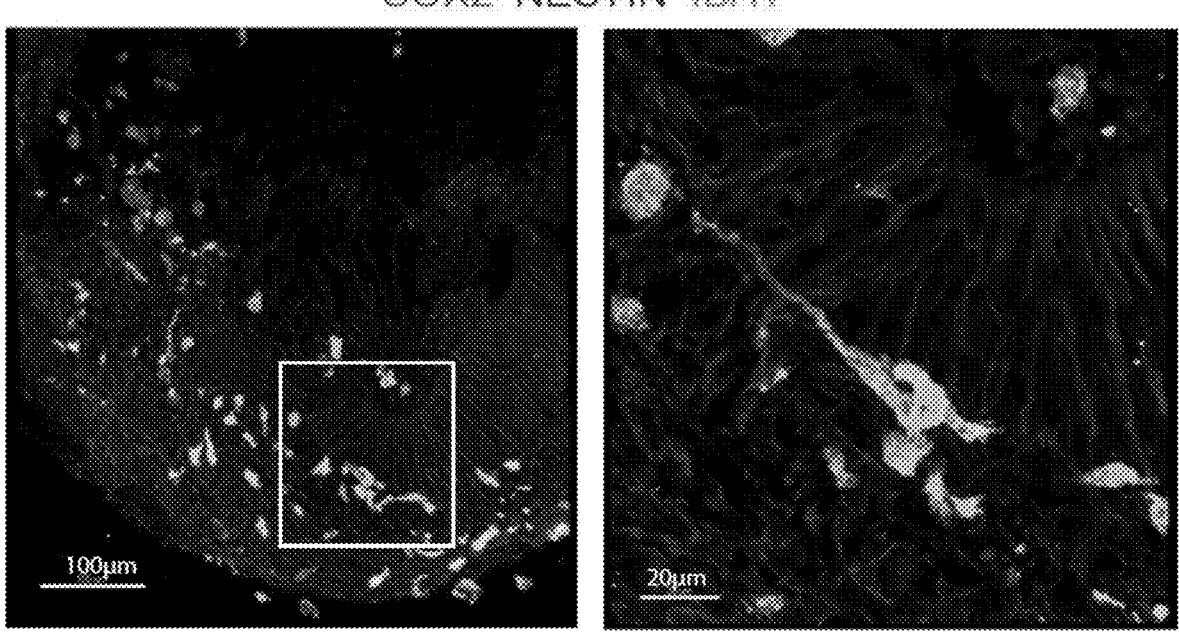
Figures 1D, 1E:
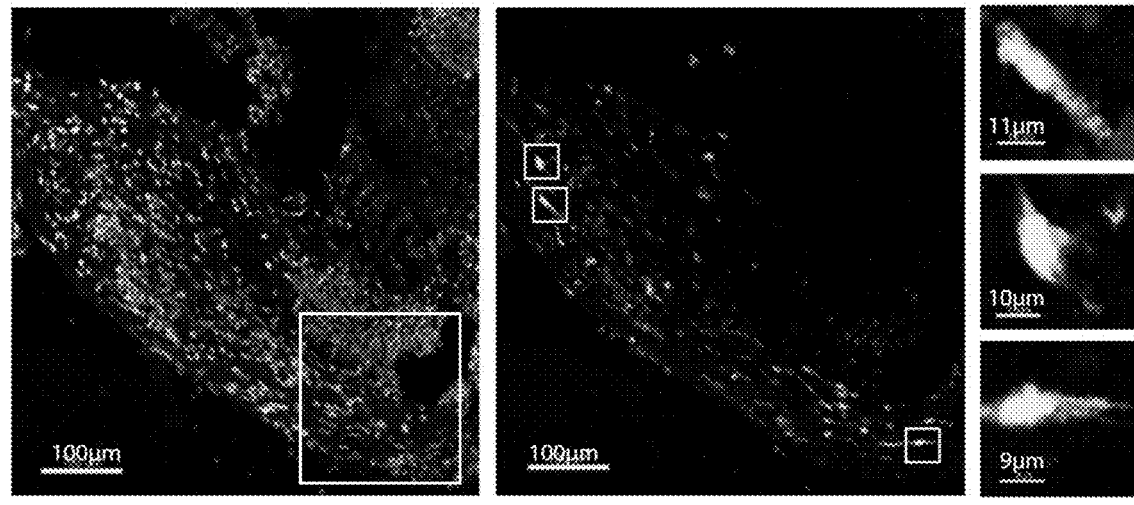

After 15 days of co-culture, it was observed that iMacs colonized the surface of the organoids as individual cells as well as in clusters (FIG. 1B). Cross-sectioned images of organoids showed that many of the iMacs were also found inside the organoids, suggesting their ability to penetrate into the organoids (FIG. 1C). Some of the iMacs found in the organoids were Ki67$^+$, suggestive of their proliferative capacity (FIG. 1D).

Figure 1F:
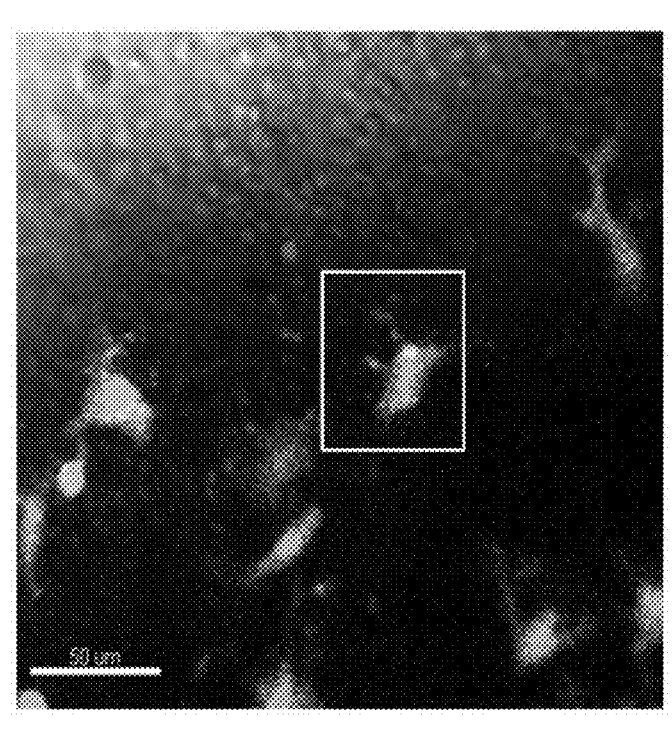
Figure 1F:
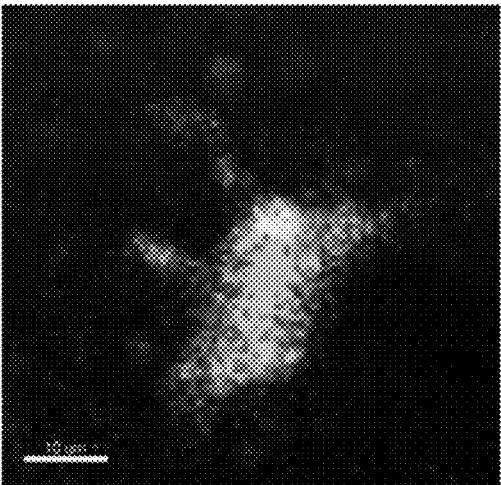

Microglia are known for their ability to respond to inflammation or injury in the brain. To test whether iMacs responded to injury in the organoids, the organoids were co-cultured with GFP$^+$ iMacs and then subjected to laser-induced neuronal injury. Live imaging showed that upon injury, GFP$^+$ iMacs started to extend their dendrites towards the injured site which is a typical behaviour of in vivo microglia towards the neuronal injury (FIG. 1E). Microglia are also known for their ability to phagocytose amyloid beta peptides which are the pathological peptides associated with Alzheimer's disease. To test whether the iMacs have the ability to phagocytose such peptides within organoids, the organoids were incubated with Fluor 555-labelled amyloid beta peptides, then co-cultured with GFP⁺ iMacs. Live imaging showed that iMacs actively moved in the organoid and were labelled with Fluor 555 signal suggesting their ability to constantly survey the organoid and phagocytose (FIG. 1F).

Together, the results suggest that iMacs in the organoids differentiate into microglia-like cells (iMicros) that survey and respond to surrounding environment similarly to in vivo microglia in the brain.

Example 2

Addition of iMacs Decrease the Size of the
Organoids and Number of Neural Progenitor Cells
(NPCs)

Figure 2A:
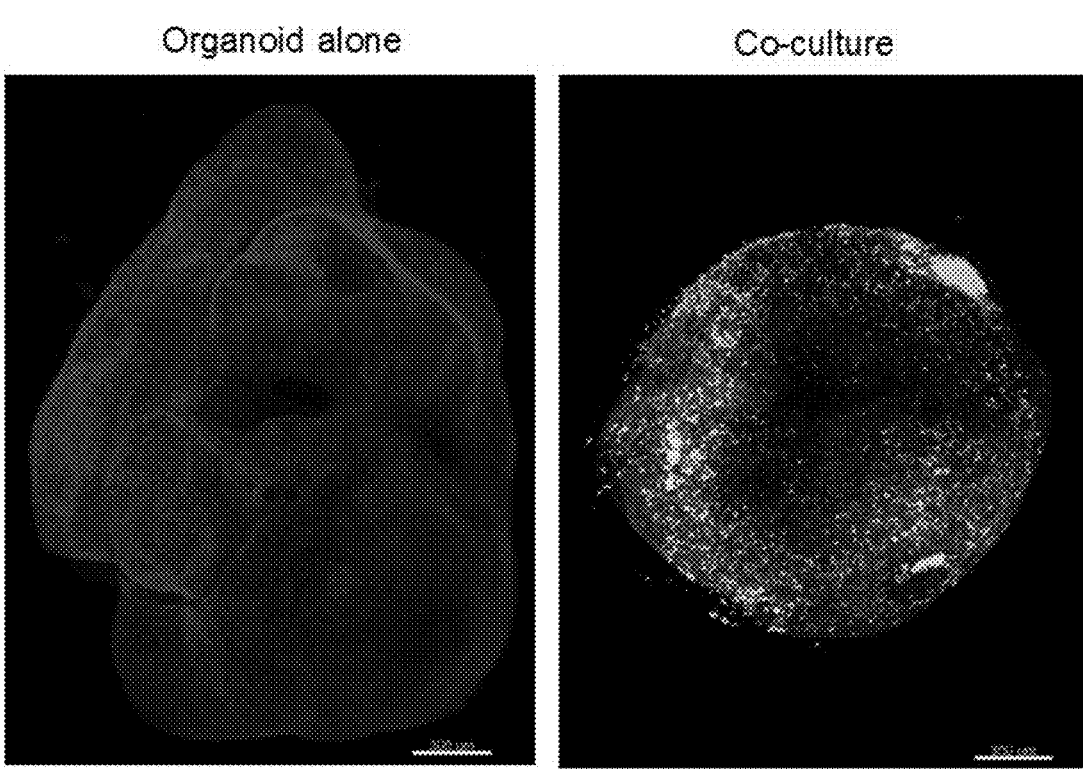
FIG. 2 shows that iMacs restrict the growth of the organoids and neural progenitor cell (NPC) number. A) shows representative 3D images of Day 44 brain organoids cultured in the absence and presence of iMacs for 18 days. The change in the size of the organoids was measured over time in the absence and presence of iMacs. B) shows flow cytometry data showing markers used to differentiate iMacs, NPCs, neurons and glial cells from the organoid. The number and % of each cell type comprising each organoid were obtained from flow cytometry.
Figure 2A:
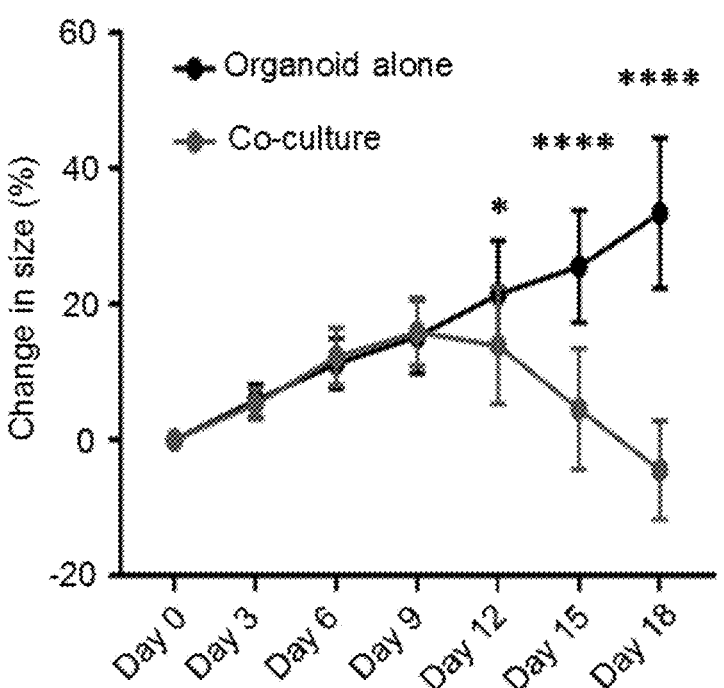
Figure 2B:
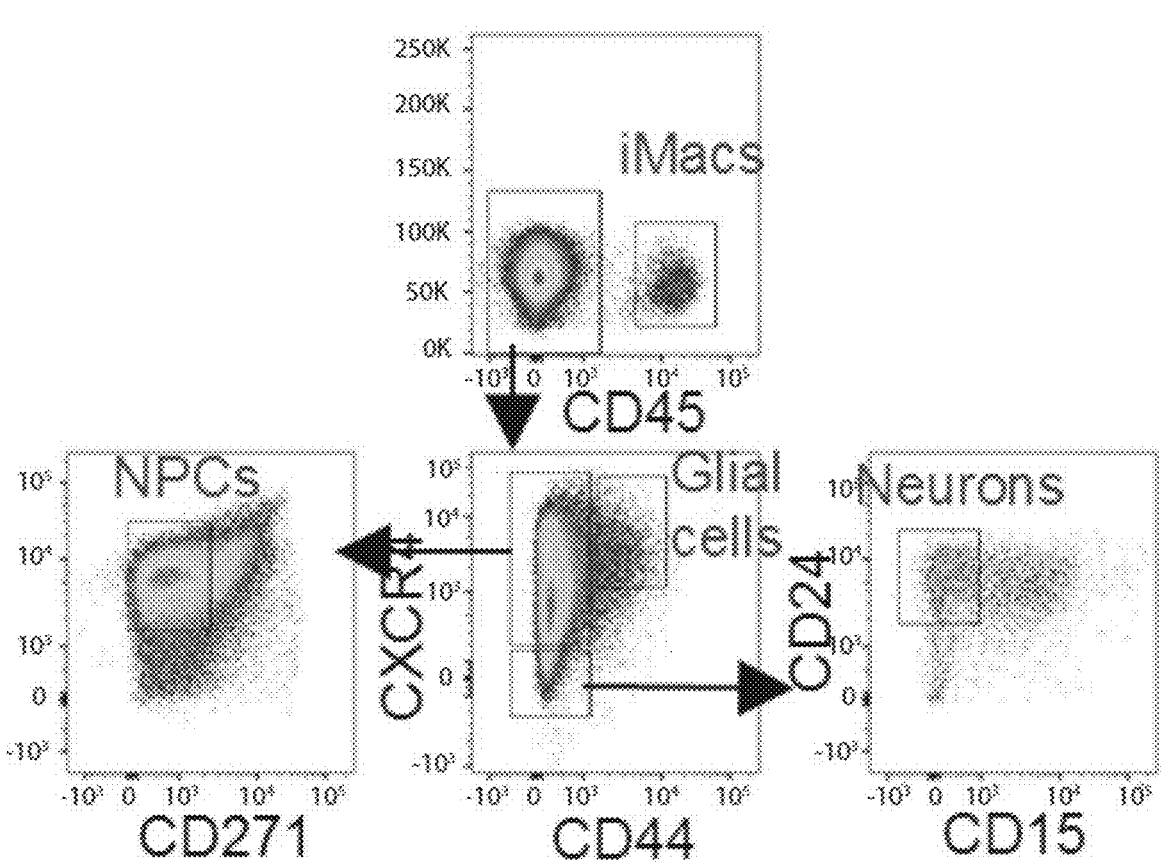
Figure 2B:
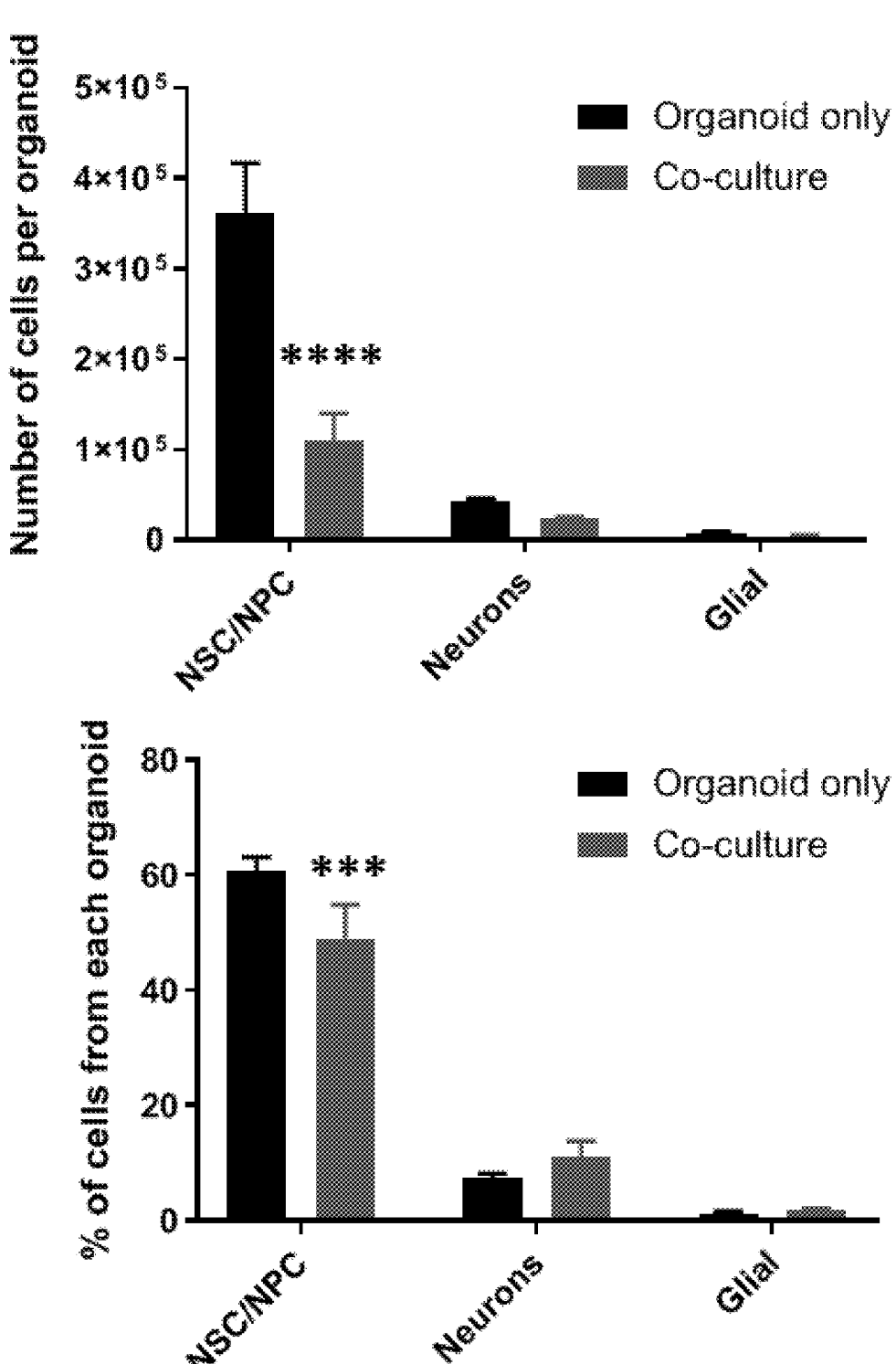
Figure 8:
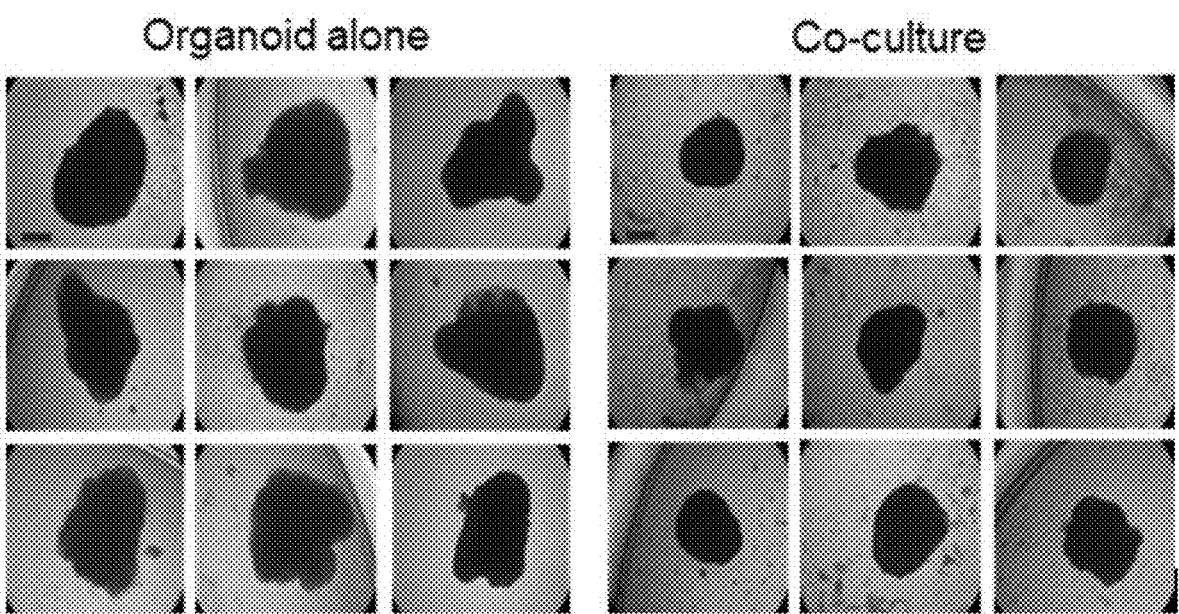
FIG. 8 shows the size of the organoids grown in the absence or presence of iMacs for 18 days.

In order to investigate the effect of iMacs on the organoid development, organoid growth throughout the co-culture was examined. The organoids showed a continuous growth in the absence of iMacs. However, when co-cultured with iMacs, the growth of the organoids was significantly reduced and they become more spherical in shape (FIG. 2A, FIG. 8). To understand if there is any change in the composition of cells in the organoids after co-culture with iMacs, the organoids were enzymatically digested and single cell suspension stained with antibodies to identify macrophages, NPCs, neurons and glial progenitor cells by flow cytometry. Importantly, number and proportion of NPCs in the organoids were reduced when the organoids were co-cultured with iMacs (FIG. 2B). This was further supported by the observation that the iMac-rich regions often lack NPCs in the organoids.

Example 3

Addition of iMacs Promote Axon Development in
the Organoids

To understand how iMicros affected brain organoid growth and NPC numbers, a single-cell RNA-seq experiment was set up that allowed the measurement of all transcriptomic changes in organoid cell in the presence or absence of macrophages. The 10× Genomics Chromium system that performs rapid droplet-based encapsulation of single cells using a gel bead in emulsion approach was used on single cell suspensions obtained from three co-cultured organoids (co-culture), three organoids cultured in the absence of iMacs (organoid alone) as well as iMacs cultured in the absence of organoids (iMac alone) (FIG. 3A).

Figures 3A, 3B:
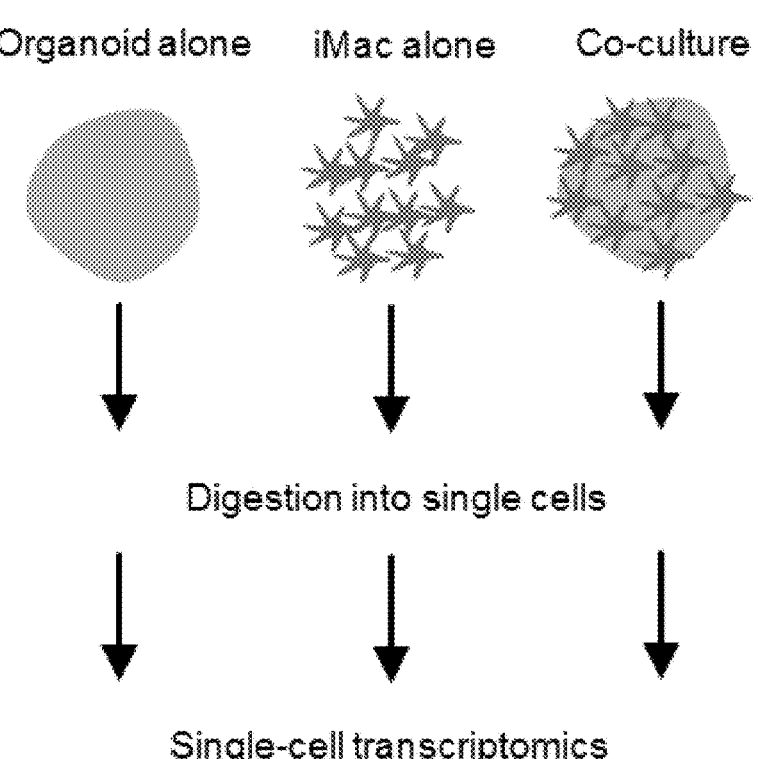
FIG. 3 shows that iMacs promotes the axonogenesis in the organoids. A) shows a schematic overview of single-cell RNA-seq experimental procedure. B) shows t-Distributed Stochastic Neighbour Embedding (t-SNE) graphs showing cells from organoids cultured in the absence (organoid alone) and presence of iMacs (co-culture). Markers were used to identify 4 main populations (NPCs, neurons, iMacs and mesenchymal cells) in the graphs. The iMac cluster from co-culture is boxed and highlighted on right. C) shows the results of GO analysis on the upregulated genes in co-cultured NPCs (co-NPCs) and co-cultured neurons (co-neurons) reveals axon development and regeneration pathways. D) is a volcano graph showing that co-NPCs upregulate axon outgrowth-related proteins, PRPH and DPYSL4. In E), immunostaining data shows that co-NPCs have more and longer axons compared to NPC alone. F) is a volcano graph showing that co-cultured iMacs (co-iMacs) upregulate genes involved in neurogenesis and axon development. G) shows the results of GO analysis on the proteins upregulated in co-iMacs reveals axon guidance pathway.
Figure 3B:
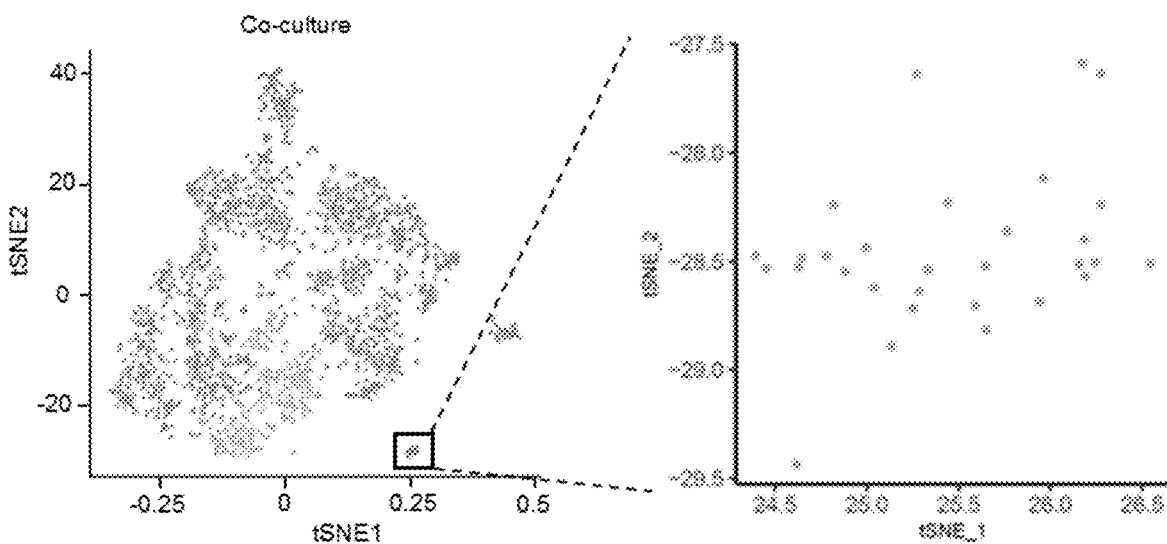
Figure 3B:
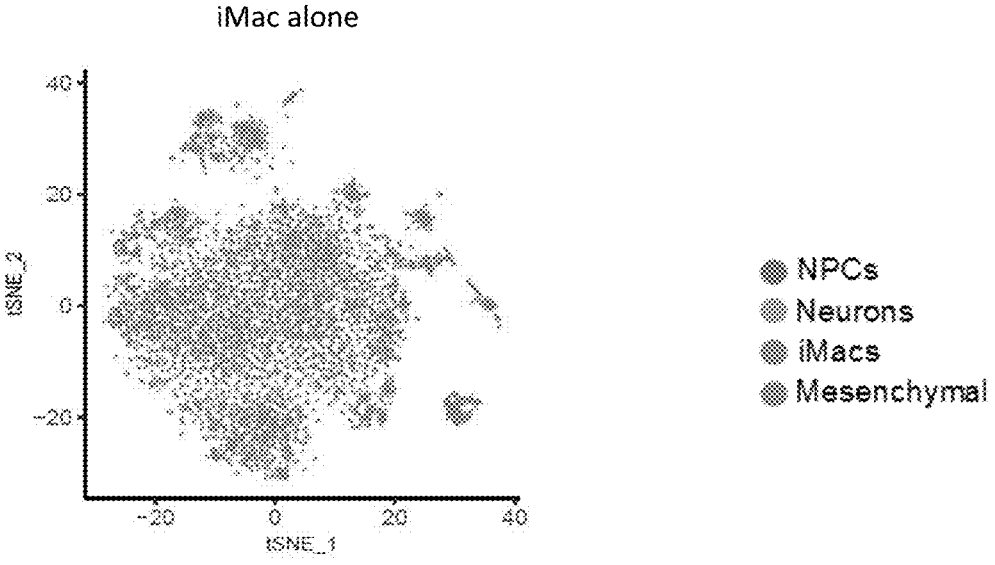

Clustering analysis was then performed on the transcriptomes, which allowed the identification of four separate cell clusters (FIG. 3B). Cluster identity were annotated by correlating with expression of neuronal markers (MYT1L, DCX, NRXN1, MAP2, TUBB), NPC markers (VIM, PAX6, SOX2, HES1), mesenchymal markers (COL1A2, COL5A1, DCN, LUM) and macrophage markers (PTPRC, AIF1, ITGAM) (FIG. 3B).

Figure 3C:
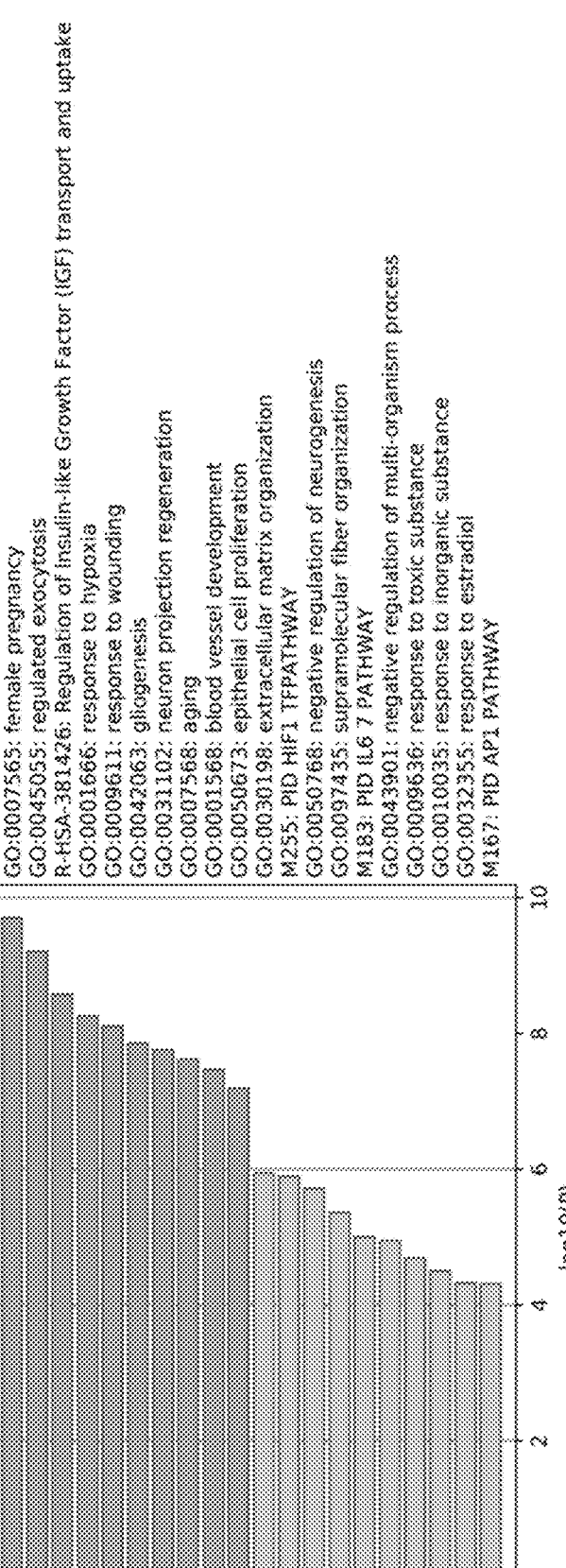
Figure 3D:
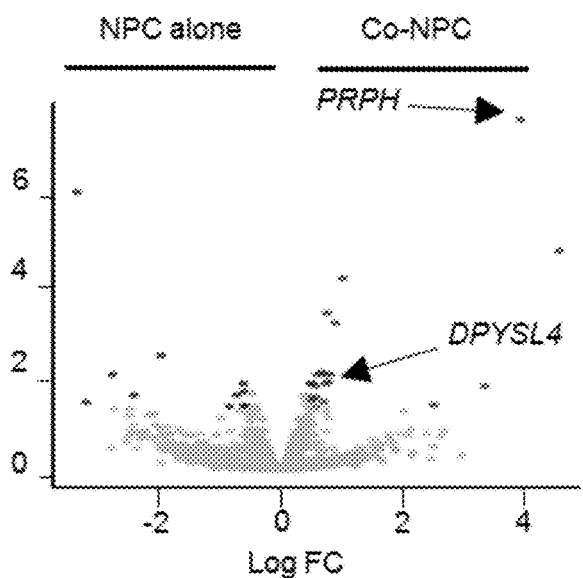

Gene ontology (GO) analysis was performed based on the differentially expressed genes (DEGs) between NPCs from organoid alone (NPC alone) and NPCs from co-cultured organoids (co-NPCs) and between neurons from organoid alone (neuron alone) and neurons from co-cultured organoids (co-neurons). The GO analysis reveals that axon development and regeneration pathways are upregulated in both co-NPCs and co-neurons (FIG. 3C). This is also supported by proteomic analysis of sorted NPCs from organoid alone versus co-cultured organoids as axonal growth-related proteins such as PRPH and DPYSL4 were upregulated in co-NPCs (FIG. 3D).

Figure 3E:
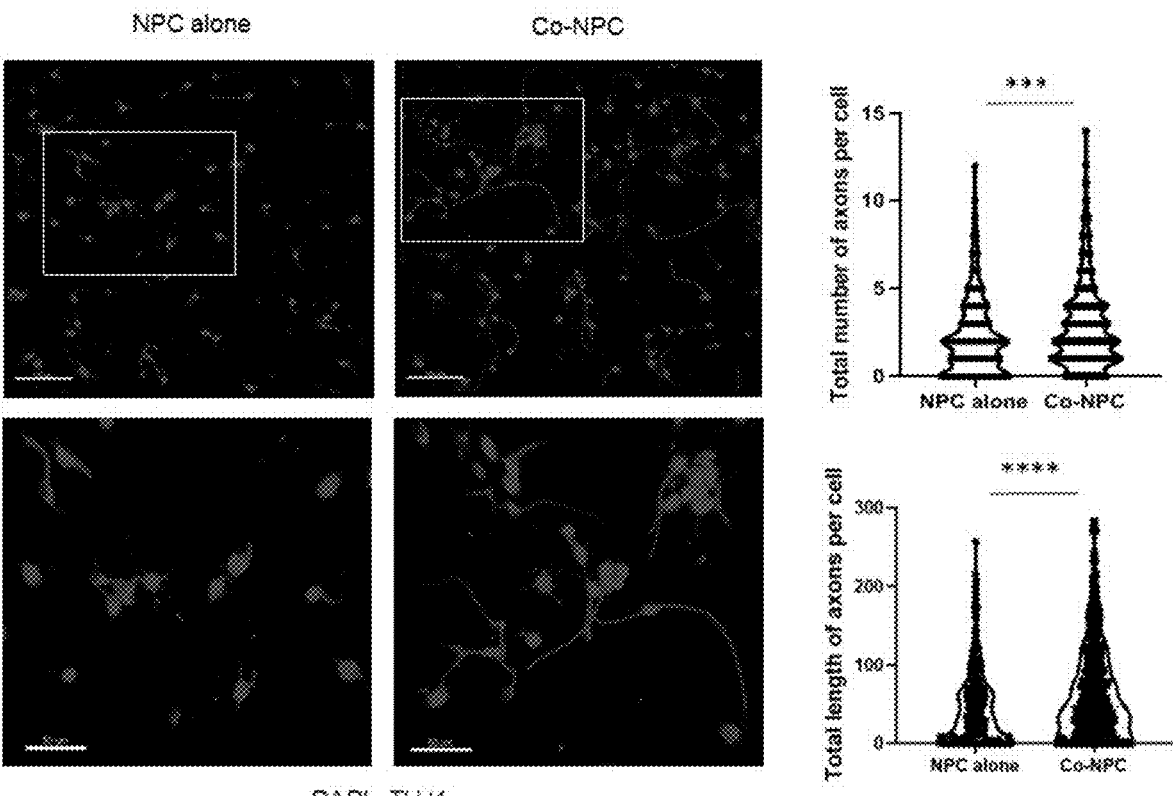
Figure 3F:
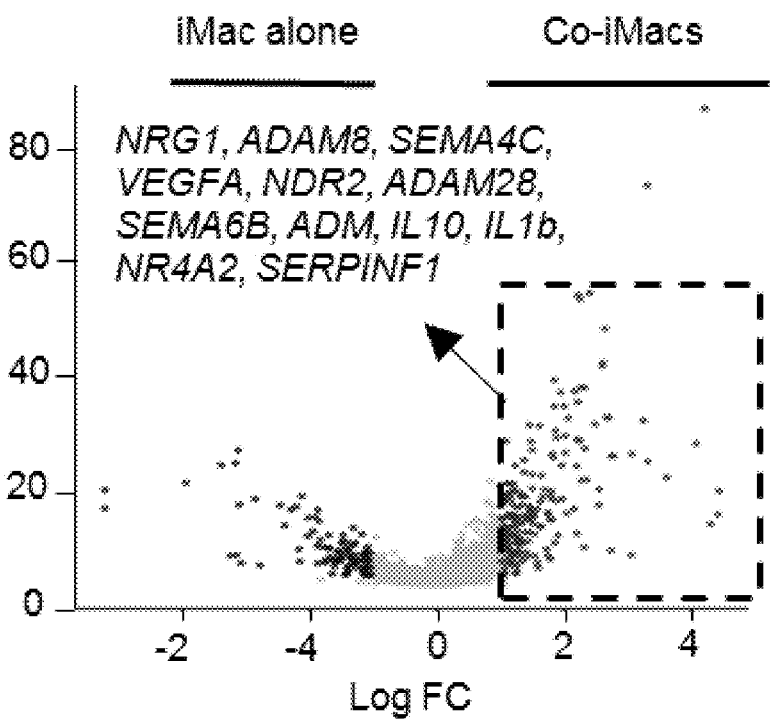

To further validate if the potential of NPCs was affected by the presence of microglia in the organoid, co-NPCs and NPC alone were sorted from the organoids and cultured in 2D for 24 hours before measuring the number and length of their axons. Co-NPCs exhibited more and longer axons than NPC alone (FIG. 3E). In line with this, iMacs in the organoids (co-iMacs) upregulated genes implicated in axon outgrowth and neurogenesis such as IL-1b, IL10, NRG1, SEMA4C, VEGFA and ADAMS (FIG. 3F).

Figure 3G:
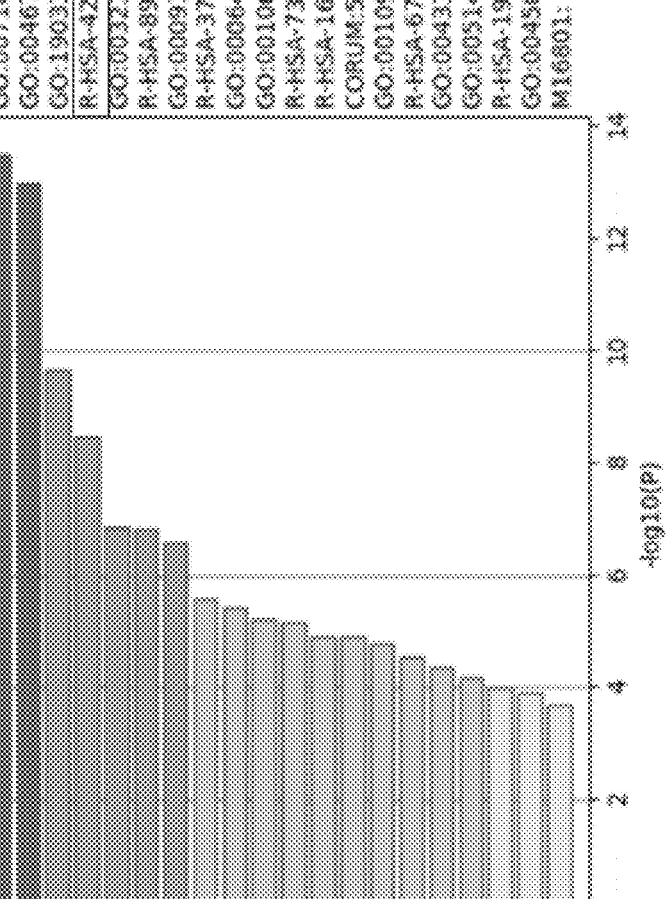

In addition, proteomic analysis of co-iMacs vs iMacs alone (FIG. 3G) suggested that co-iMacs upregulate proteins involved in axon guidance.

Example 4

Co-iMacs and Embryonic Microglia Express PLIN2
and Lipid Droplets

Figure 4A:
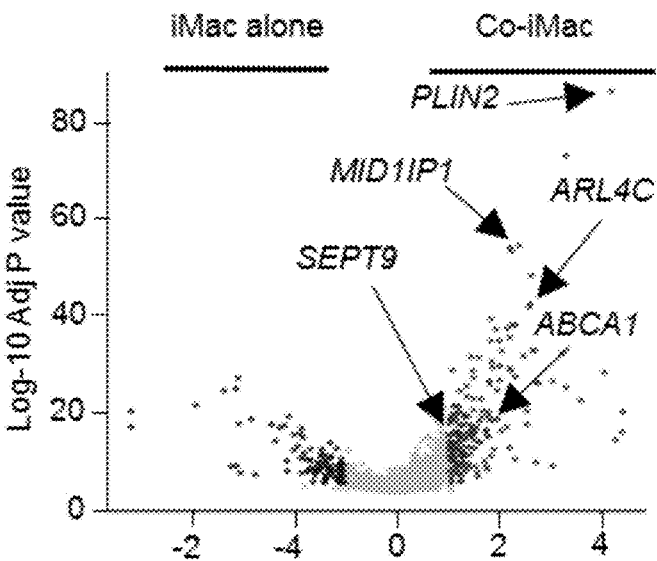
FIG. 4 shows that iMacs and embryonic microglia express PLIN2 and lipid droplets. A) is a volcano graph showing genes involved in lipid droplet formation and lipid export upregulated in co-iMacs. B) shows the live imaging of co-iMacs that contain lipid droplets. C) shows co-iMacs expressing lipid droplets and PLIN2 in the organoid. Arrowheads, the overlap between PLIN2 and lipid droplets in iMacs. D) shows microarray data showing PLIN2 is expressed in microglia only during early stage of mouse brain development. E) shows immunostaining showing lipid droplets and PLIN2 expressed in mouse embryonic microglia (E13.5). F) shows immunostaining showing lipid droplets and PLIN2 expressed in human embryonic microglia (15 weeks).
Figure 4B:
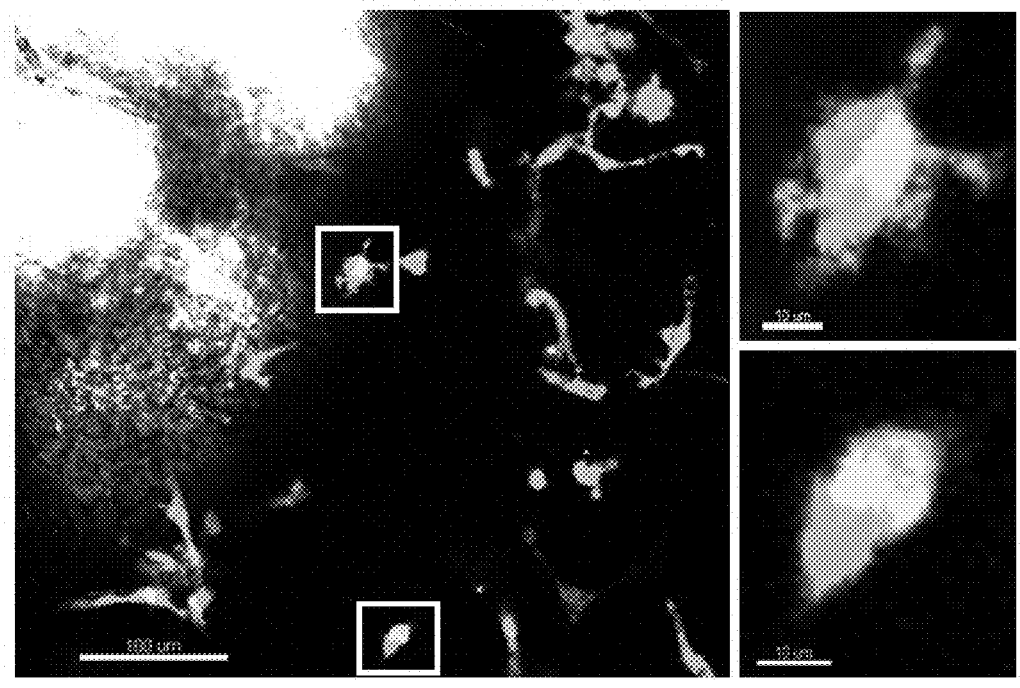
Figure 4C:
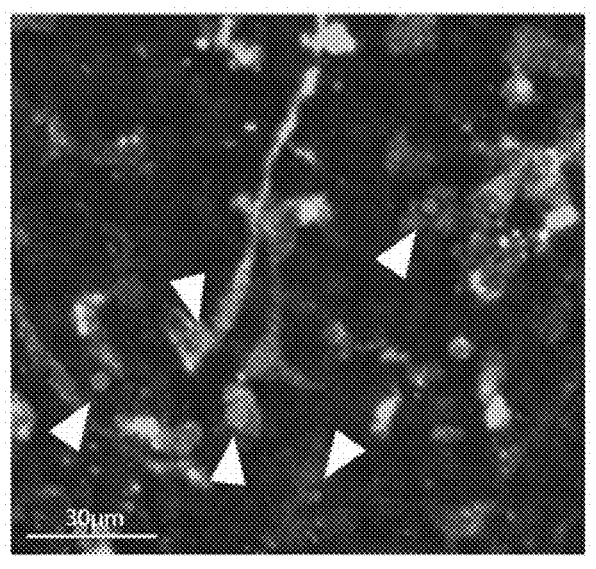
Figure 4C:
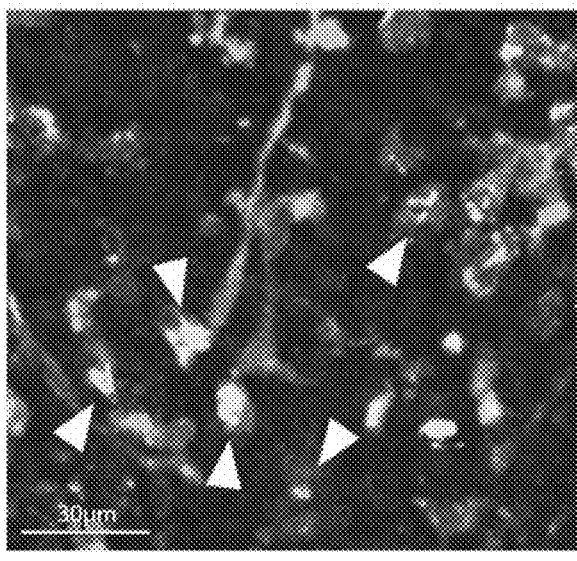
Figure 4D:
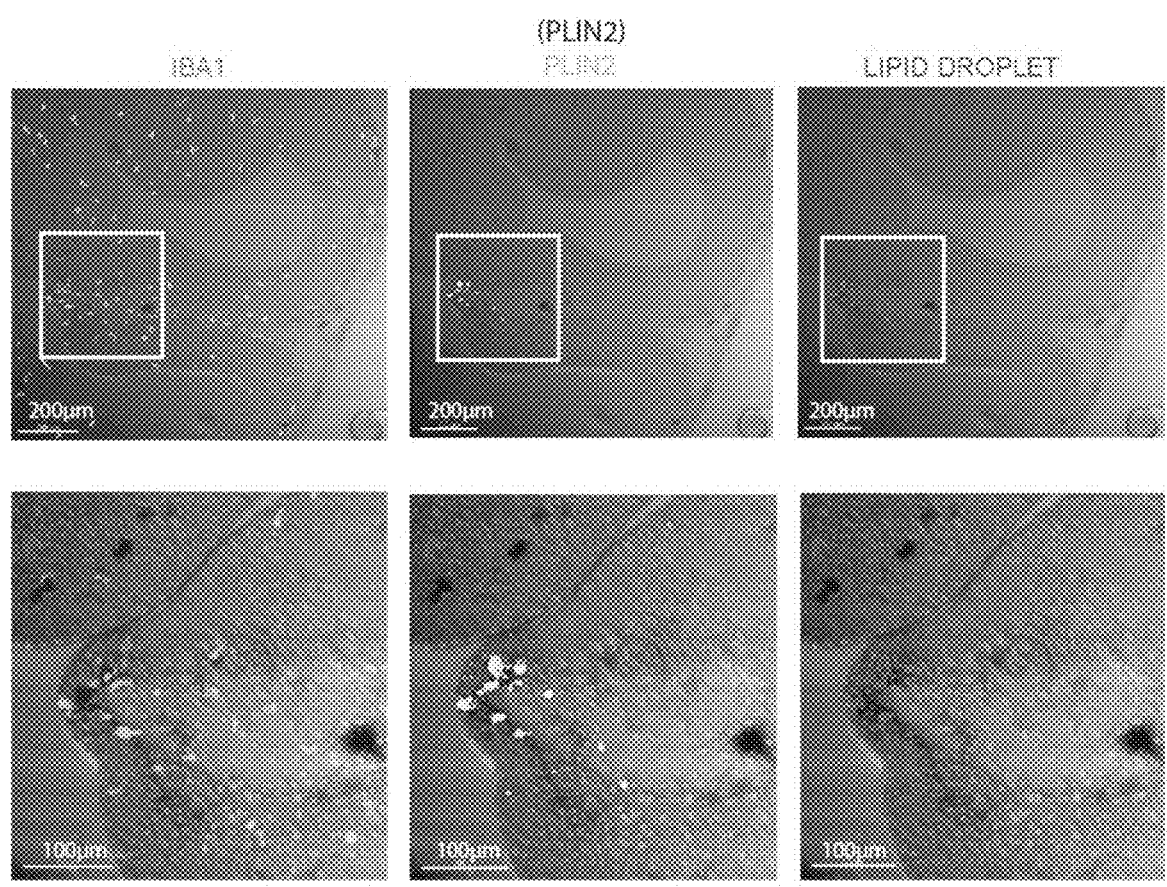
Figure 4E:
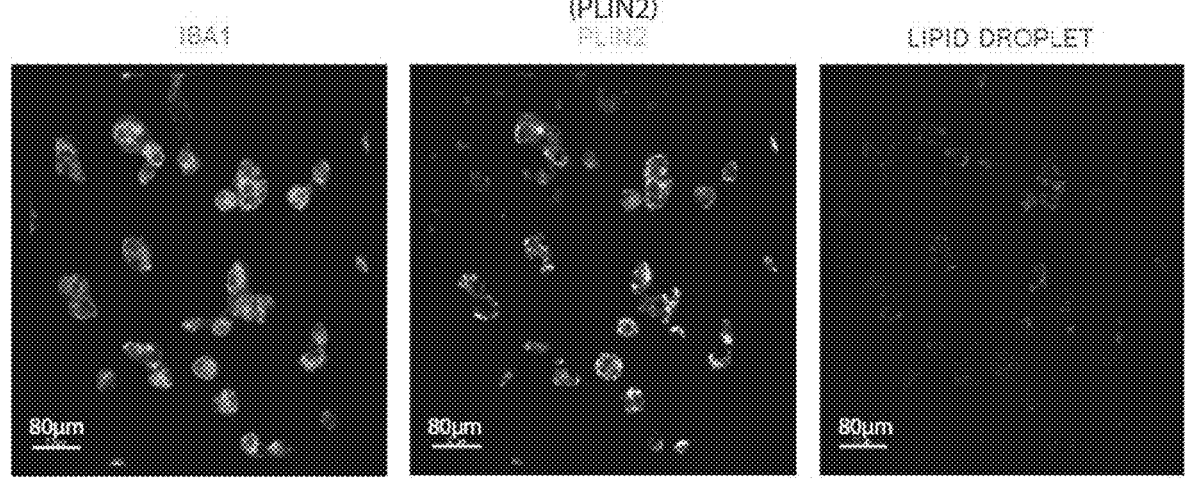

The analysis of DEGs between co-iMac and iMac alone revealed that Perilipin 2 (PLIN2) that is known to be involved in lipid droplet formation was among the top upregulated DEGs in the co-iMacs. In addition, other genes such as M1D1LP1, ARL4C, SEPT9 and ABCA1 that are involved in lipid droplet formation and lipid export were found to be upregulated in co-iMacs (FIG. 4A). Live imaging show that many of the co-iMacs contain lipid droplets (FIG. 4B) and immunostaining revealed that the expression of PLIN2 and lipid droplets was mostly restricted to co-iMacs, but not in other cell types in the organoids (FIG. 4C). Similarly, lipid droplets and PLIN2 expression were observed exclusively in microglia in embryonic mouse and human brains (FIGS. 4D and 4E). However, their expression was not observed in microglia in adult mouse and primate brains (data no shown). This suggested that the co-iMacs and embryonic microglia might play a central role in driving the metabolic changes in neuronal cells which might be essential for brain development.

Example 5 iMacs Affects the Lipid Contents and Metabolism
of the Cells in the Organoids

Figure 5A:
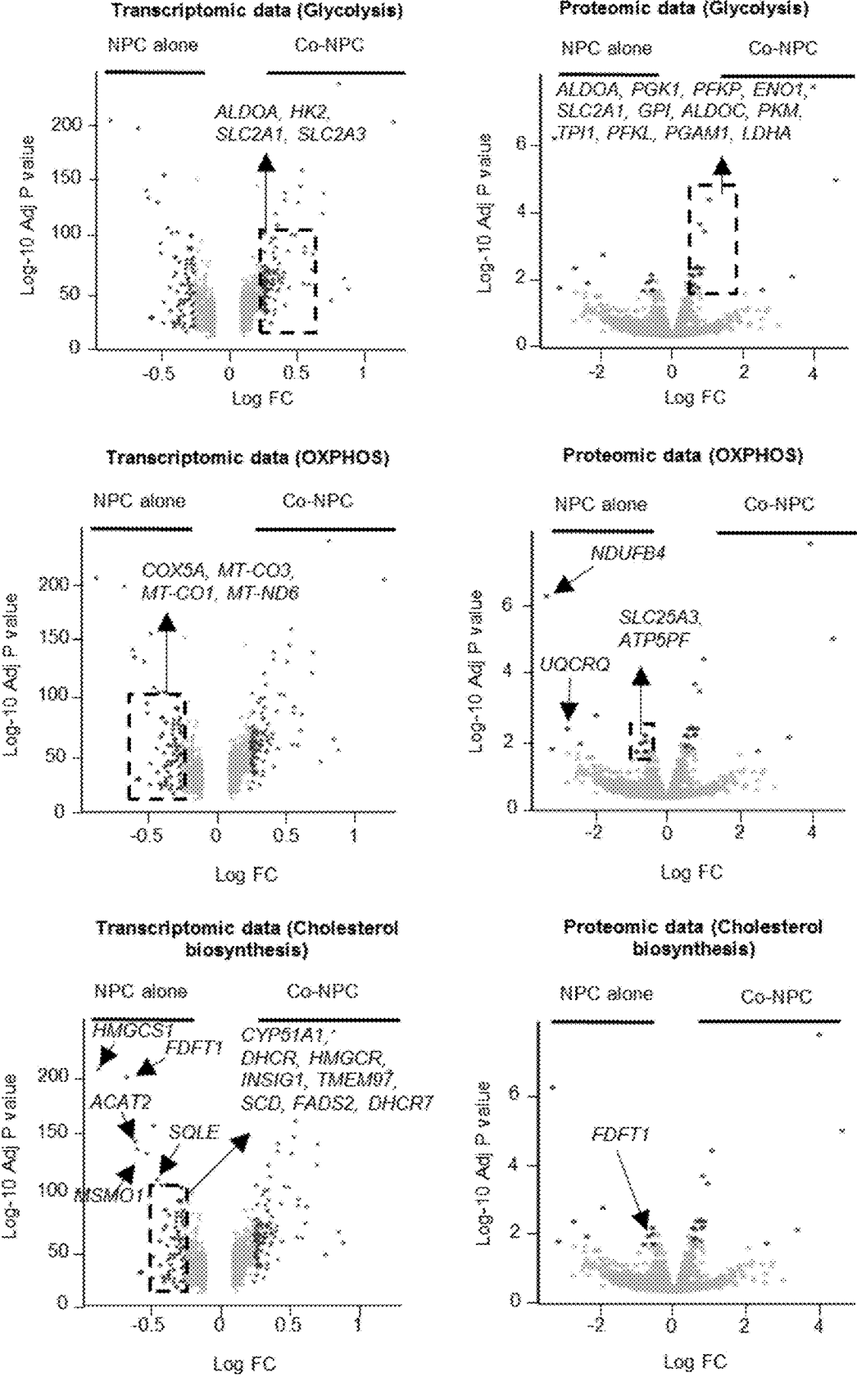
FIG. 5 shows that iMacs affect the lipid contents and metabolism of the cells in the organoids. A) depicts volcano graphs showing changes in the expression level of genes and proteins involved in glycolysis, OXPHOS and cholesterol biosynthesis in co-NPCs. B) shows the results of GO analysis indicating the cholesterol biosynthesis pathway as the most significantly downregulated pathway in co-NPCs. C) shows that more lipid droplets are found in the co-cultured organoid. D) shows flow cytometry data showing that the co-NPCs contain a higher lipid contents compared to the NPC alone. E) shows the data from mass spectrometry-based lipidomics showing a higher level of CE, DAG and TAG in co-NPCs.
Figure 5B:
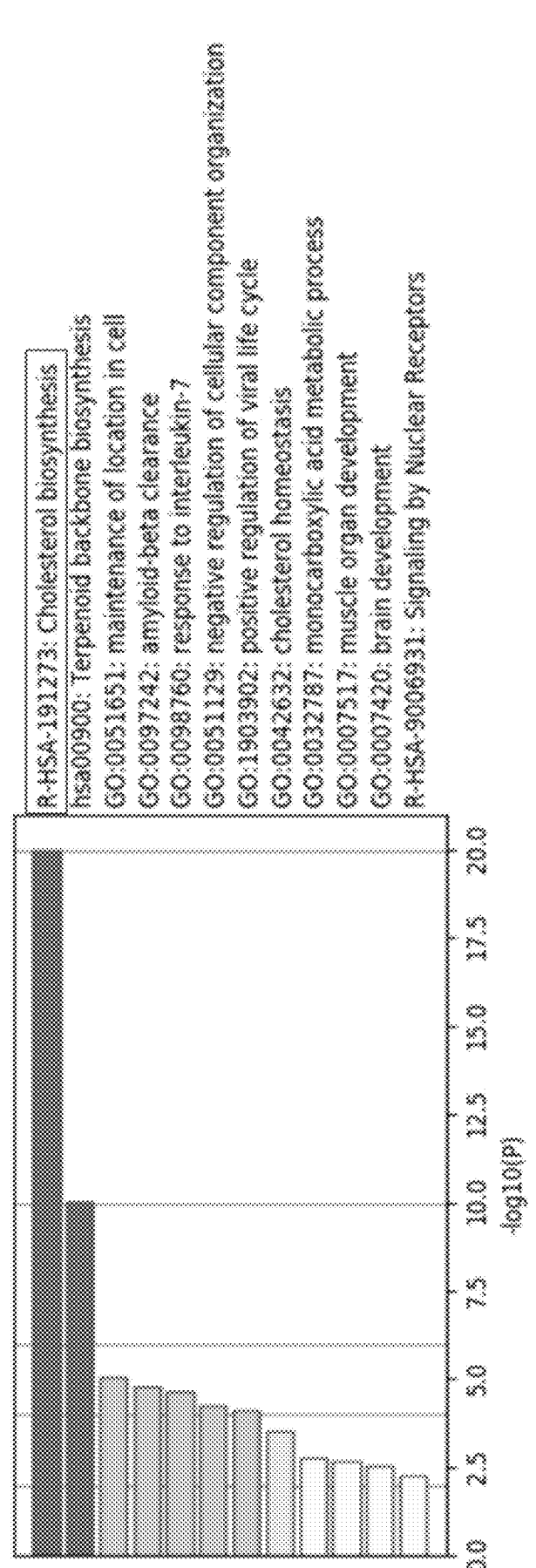

Further analysis of DEGs between co-NPCs and NPCs revealed that the majority of DEGs were genes involved in metabolic pathways such as glycolysis, OXPHOS and importantly cholesterol biosynthesis (FIG. 5A). This was further validated by proteomic analysis (FIG. 5A). Gene ontology (GO) analysis revealed that the cholesterol biosynthesis pathway was the most significantly downregulated pathway in co-NPCs (FIG. 5B).

Figure 5C:
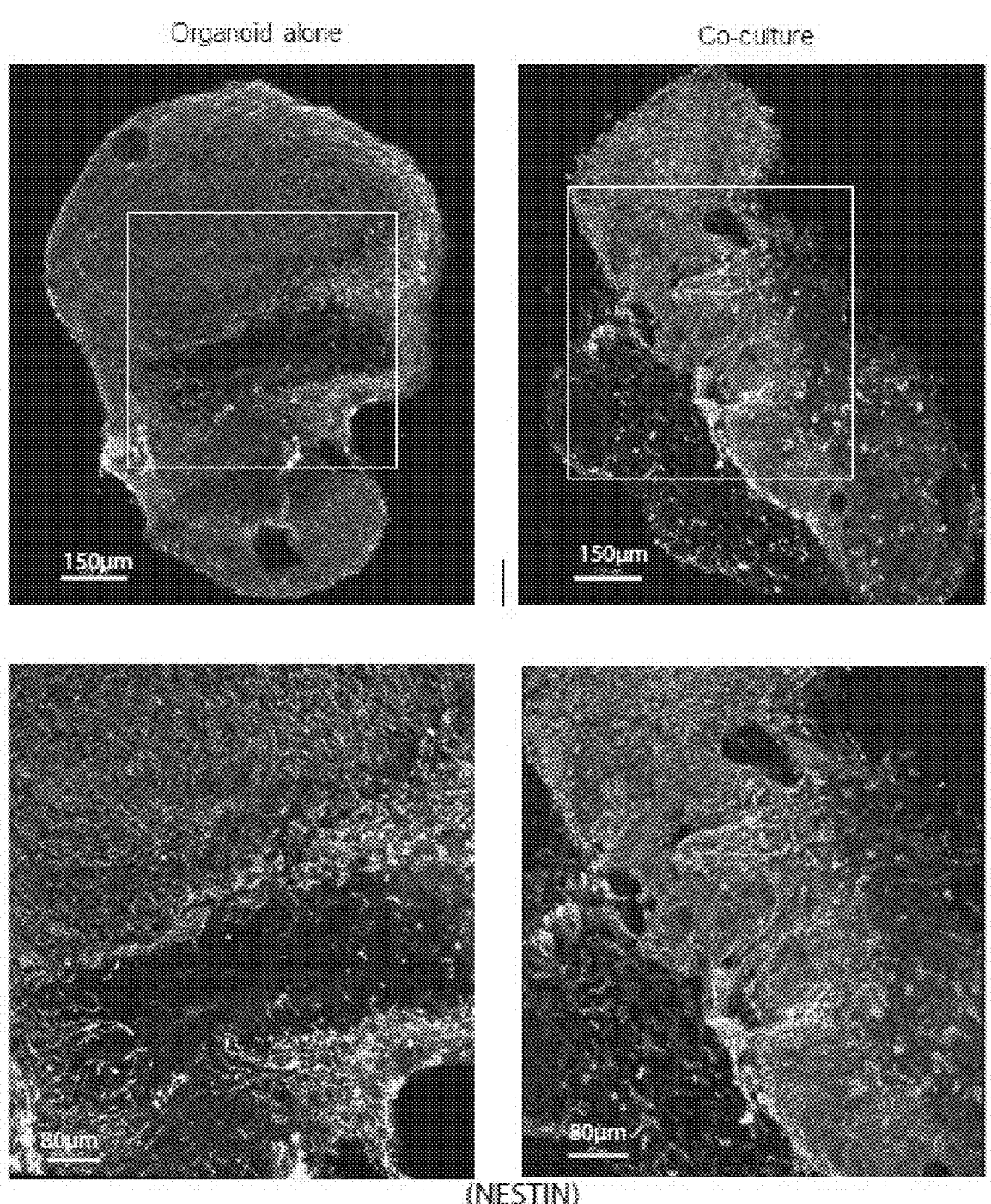
Figures 5D, 5E:
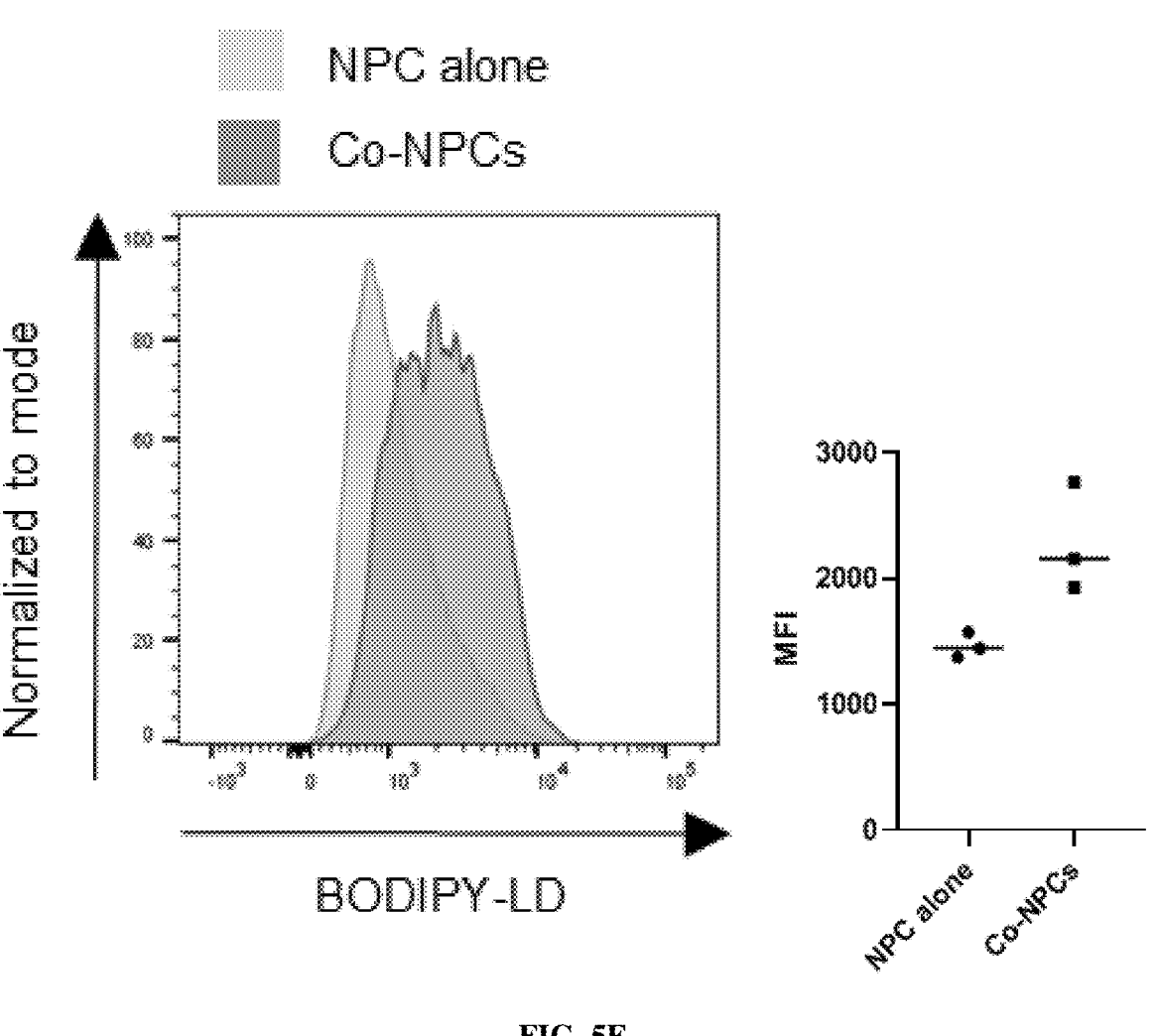

Given that the high intracellular level of cholesterols usually leads to the downregulation of genes involved in cholesterol biosynthesis, a study was carried out to investigate whether there is any increase in the lipid contents in co-NPCs after co-culture with iMacs. BODIPY™ 493/503 staining (which stains neutral lipids) on the cross-sectioned organoids revealed that more lipid droplets were present in the co-cultured organoids as compared to the organoid alone and were distributed more widely within the organoids (FIG. 5C). Next, the organoids were digested into single cells and stained them with BODIPY™ 493/503 for flow cytometry analysis. The flow cytometry data indicated that the neutral lipid content is higher in co-NPCs in comparison with NPC alone (FIG. 5D). In order to further validate this, mass spectrometry-based lipidomics was conducted to quantify the lipids in co-NPCs and NPC alone. The data suggested that there are more neutral lipids such as diacylglycerols (DAG), triacylglycerols (TAG) and cholesteryl esters (CE) in co-NPCs as compared to NPC alone (FIG. 5E). Together, the data suggested that the addition of iMacs modified the lipid distribution in the organoids and particularly the lipid content in NPCs.

Example 6 iMacs Transport Cholesterol to the Cells in the Organoids

Figure 6A:
FIG. 6 shows that there is cholesterol transportation from iMacs to the cells in the organoids. A) depicts flow cytometry data and immunostaining showing that iMacs take up the BODIPY-CE and store them in lipid droplets. B) depicts flow cytometry data showing BODIPY-CE found in the cells in the organoids after co-culture with iMacs for 7 days. C) shows that co-NPCs sorted from organoid contain BODIPY-CE.
Figure 6A:
Figure 6B:
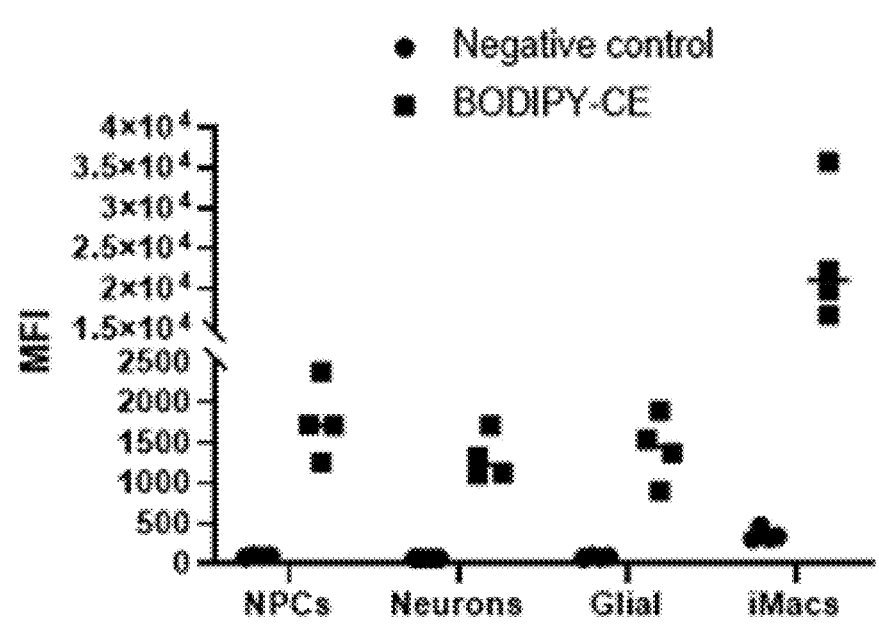
Figure 6C:
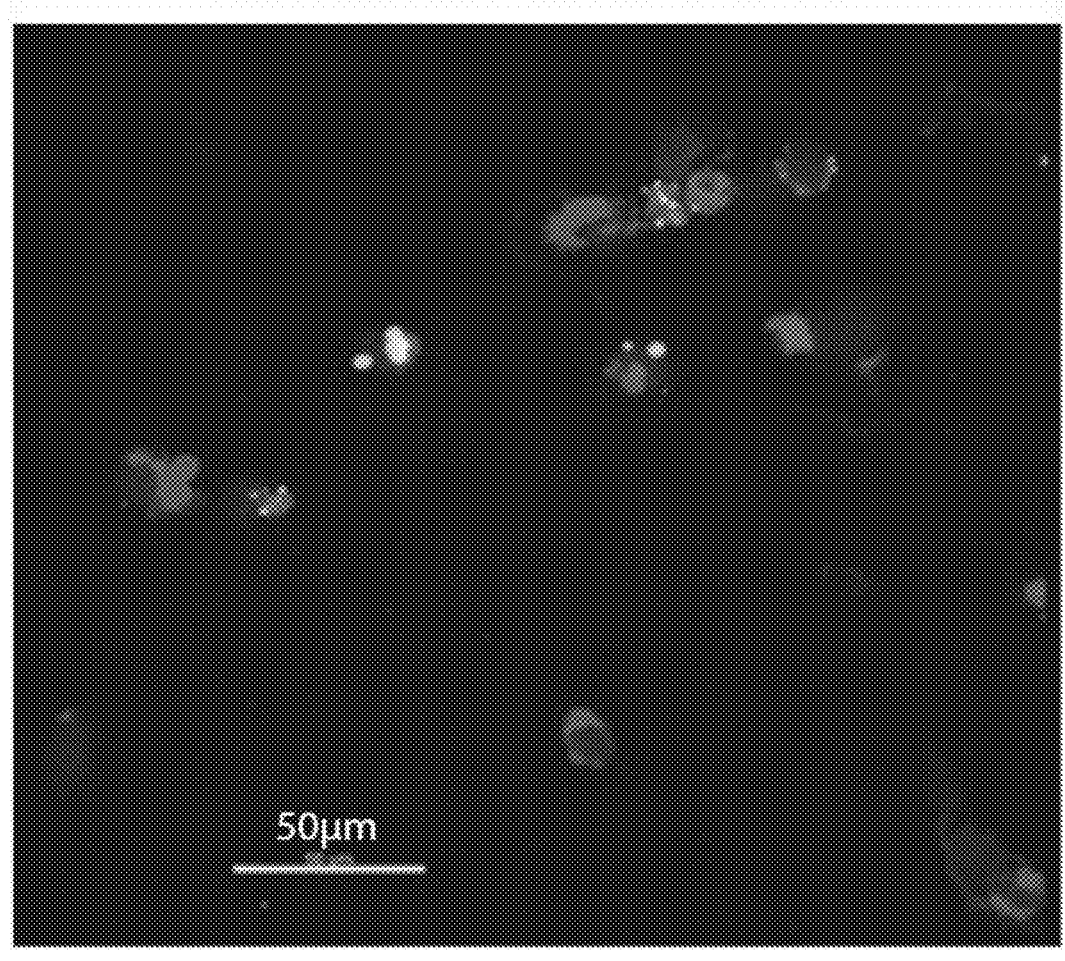
Figure 7:
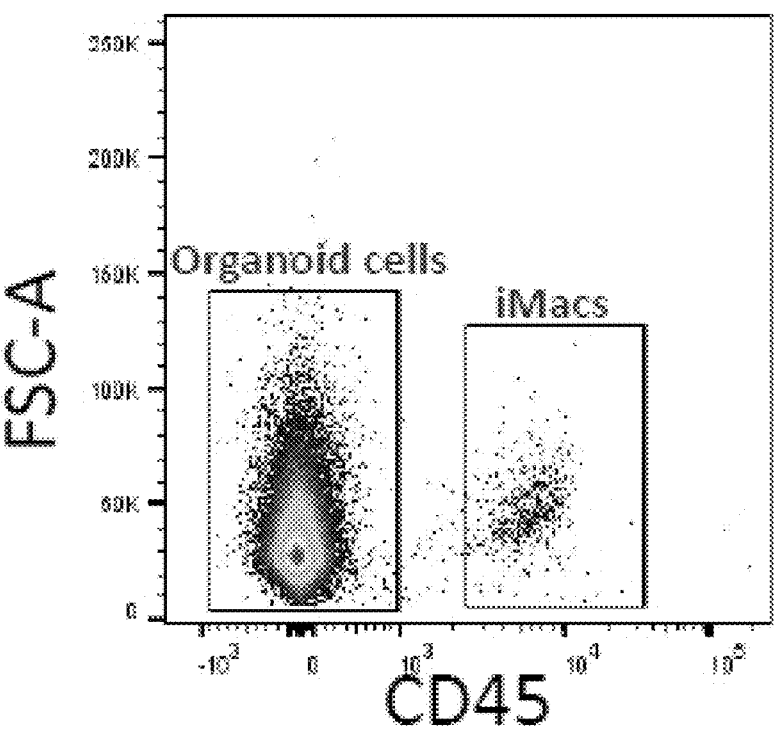
FIG. 7 shows that accutase and collagenase treatment releases more live cells from the organoids that accutase treatment alone. Accutase has commonly been used in previous studies for the digestion of the organoids. Organoids co-cultured with iMacs for 15 to 21 days were treated with either accutase only or with accutase and collagenase. The use of accutase together with collagenase allows more iMacs and other cell types to be sorted from the organoids using fluorescence activated cell sorting (FACS) for bulk-RNA-seq and other downstream experiments such as single cell analysis, 2D culture of NPCs.
Figure 7:
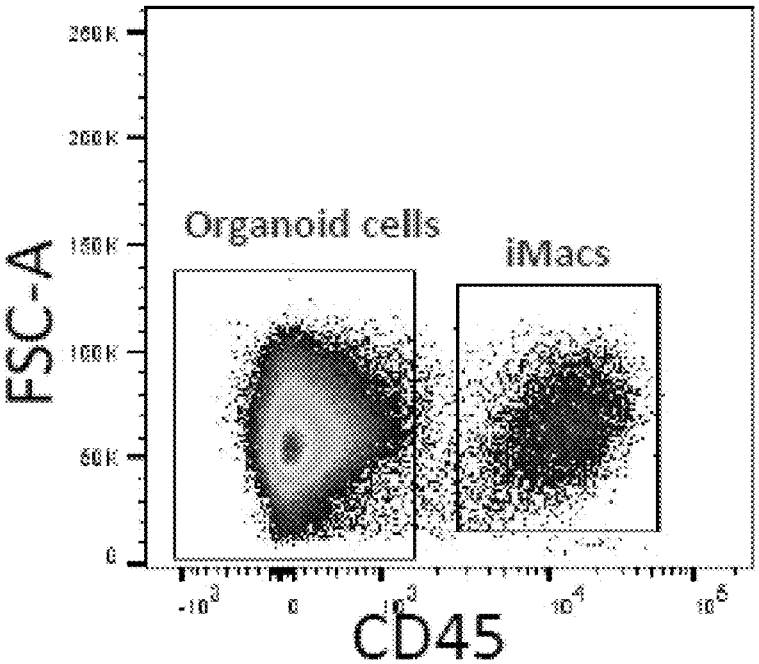
Figure 7:
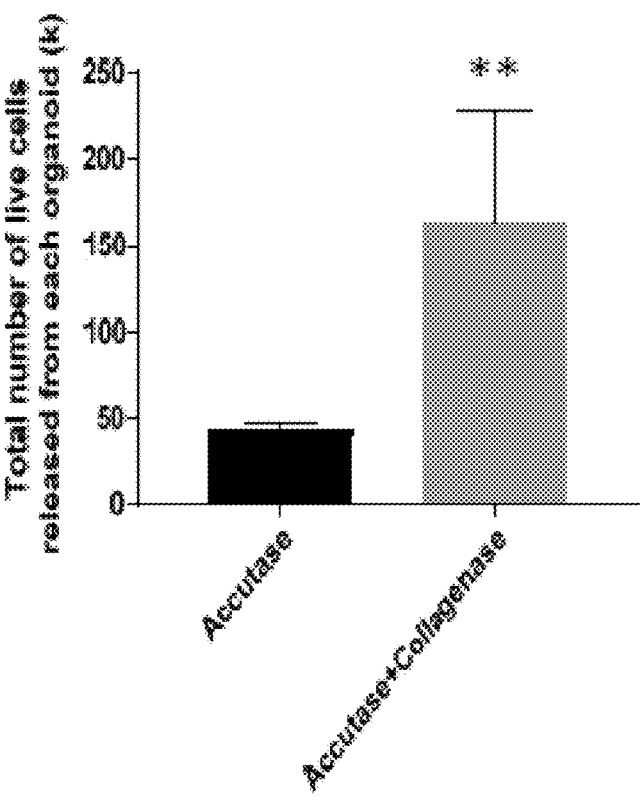
Figure 7:
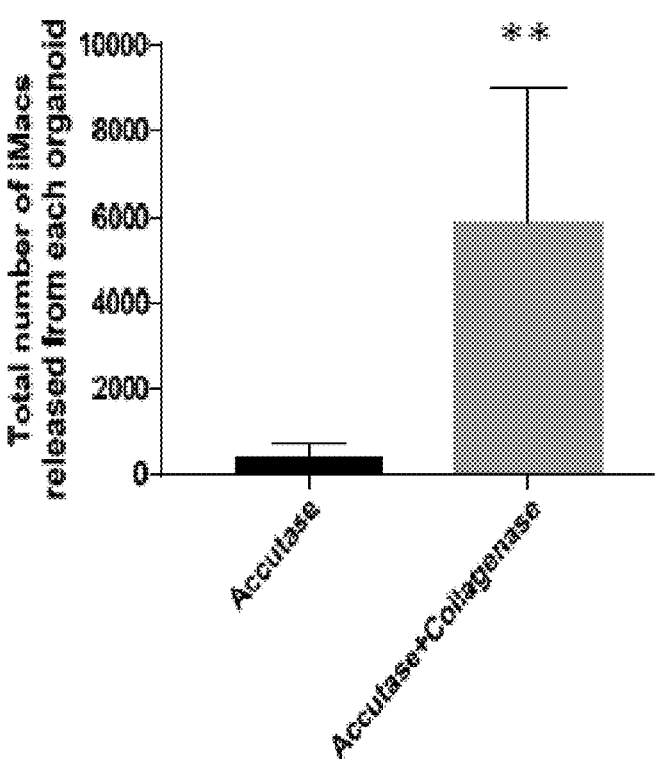

Astrocytes are known to be the primary cell population in the adult brain that synthesizes and metabolizes lipids. It was shown that the cultured neurons from mammalian central nervous system require astrocyte-derived cholesterol to form numerous and efficient synapses. However, astrocytes are not present in early stage of brain development. Thus, such function may be played by microglia during early development. To examine whether there is any transportation of cholesterols from co-iMacs to co-NPCs in the organoids, iMacs were cultured with green fluorescent BODIPY® FL C12 cholesteryl ester (BODIPY-CE) overnight and were washed three times with PBS before co-culturing with the organoids. Immunostaining showed that iMacs took up the BODIPY-CE and store them in lipid droplets as indicated by the overlap with PLIN2 proteins (FIG. 6A). The BODIPY-CE-containing iMacs were then co-cultured with organoids for 7 days and performed flow cytometry analysis on the organoids. The flow cytometry data suggested that NPCs, neurons and glial cells in the organoids contain BODIPY-CE (FIG. 6B). To further confirm this, co-NPCs from the organoids were sorted and subjected to immunostaining. The images clearly showed that CE-FITC are found inside the co-NPCs (FIG. 6C). Together, the data suggest that there is a transportation of cholesterol from iMacs to the cells in the organoids.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for generating a microglia-sufficient brain organoid having functionally active microglia cells, comprising a step of incubating primitive-like macrophage cells with a brain organoid that is between 23 days old to 29 days old in cerebral organoid medium comprising CSF-1 in a low attachment cell culture vessel to generate functionally active microglia cells, wherein:

a) the primitive-like macrophage cells are generated from a first population of stem cells by:

i) incubating said stem cells in a culture medium comprising a GSK3 inhibitor, BMP4, and VEGF to differentiate said stem cells into cells of a mesoderm lineage;

ii) incubating said cells of the mesoderm lineage in a culture medium comprising FGF-2 to differentiate said cells of the mesoderm lineage into hemangioblast cells;

iii) incubating said hemangioblast cells in a culture medium comprising VEGF and FGF-2;

iv) incubating said hemangioblast cells in a culture medium comprising DKK1, SCF, FGF2, IL3, and IL6 to differentiate said hemangioblast cells to hematopoietic cells;

v) incubating said hematopoietic cells in a culture medium comprising SCF, FGF-2, IL-3, and IL-6 to induce maturation of said hematopoietic cells;

vi) incubating said matured hematopoietic cells in a culture medium comprising CSF-1 to differentiate said matured hematopoietic cells to primitive-like macrophage cells; and b) the brain organoid is generated from a second population of stem cells over a period of between 23 to 29 days by:

i) incubating said second population of stem cells in a low attachment cell culture vessel to form an embryoid body;

ii) incubating said embryoid body in neural induction medium to differentiate said embryoid body into an organoid comprising neuroectoderm cells;

iii) embedding the organoid comprising neuroectoderm cells in Matrigel and incubating the organoid comprising neuroectoderm cells in cerebral organoid medium containing N2 and B27 without vitamin A to differentiate said organoid comprising neuroectoderm cells to an organoid comprising neural epithelial cells;

iv) incubating the organoid comprising neural epithelial cells with cerebral organoid medium containing N2 and B27 without vitamin A to differentiate said organoid comprising neural epithelial cells to said brain organoid.

2. The method of claim 1, wherein the brain organoid is about 26 days old.

3. The method of claim 1, wherein the cerebral organoid medium comprises about 25-100 ng/ml CSF-1.

4. The method of claim 1, comprising incubating about 150,000 or less primitive-like macrophages with the brain organoid.

5. The method of claim 1, comprising incubating the primitive-like macrophage cells and brain organoid together for at least 1 week.

6. The method of claim 5, further comprising a step of dissociating cells of the microglia-sufficient brain organoid and isolating one or more predetermined populations of cells.

7. The method of claim 6, comprising isolating the one or more predetermined populations of cells using fluorescence activated cell sorting (FACS) or magnetic activated cell sorting (MACS).

8. The method of claim 1, comprising generating the primitive-like macrophages over a period of 26 days.

9. The method of claim 1, comprising generating the brain organoid over a period of about 26 days.

10. The method of claim 1, wherein the first and second populations of stem cells are embryonic stem cells (ESC), induced pluripotent stem cells (iPSC), or combinations thereof.

* * * * *